United States Patent [19]

Cragoe, Jr. et al.

[11] Patent Number: 4,778,897

[45] Date of Patent: Oct. 18, 1988

[54] 6H-DIBENZ[B,E][1,4]OXATHIEPIN COMPOUNDS

[75] Inventors: Edward J. Cragoe, Jr., Lansdale; Clarence S. Rooney, Worcester, both of Pa.; Joshua Rokach, Chomedey Laval, Canada

[73] Assignee: Merck & Co., Inc., Rahway, N.J.

[21] Appl. No.: 55,105

[22] Filed: May 28, 1987

Related U.S. Application Data

[60] Division of Ser. No. 817,373, Jan. 9, 1986, Pat. No. 4,699,917, which is a continuation-in-part of Ser. No. 238,097, Feb. 25, 1981, abandoned, which is a continuation of Ser. No. 930,103, Aug. 1, 1978, abandoned.

[51] Int. Cl.$^4$ ............................................. C07D 417/04
[52] U.S. Cl. .................................................. 548/135
[58] Field of Search ....................... 549/10; 548/135; 514/362, 431

[56] References Cited

U.S. PATENT DOCUMENTS 4,622,403 11/1986 Williams et al. ................ 548/135

Primary Examiner—John M. Ford
Assistant Examiner—Kurt G. Briscoe
Attorney, Agent, or Firm—Hesna J. Pfeiffer; Charles M. Caruso

[57] ABSTRACT

Novel 6H-dibenz[b,e][1,4]oxathiepin derivatives of the formulae I and Ia are employed in the treatment and control of allergic conditions such as allergic asthma.

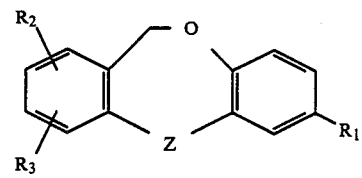

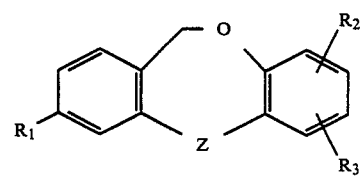

9 Claims, No Drawings

6H-DIBENZ[B,E][1,4]OXATHIEPIN COMPOUNDS

CROSS REFERENCE TO RELATED APPLICATIONS

This is a division of application Ser. No. 817,373, filed Jan. 9, 1986, now U.S. Pat. No. 4,699,917 which is a continuation-in-part of Ser. No. 238,097 filed Feb. 25, 1981, now abandoned, which was a continuation of Ser. No. 930,103, filed Aug. 1, 1978, now abandoned.

BACKGROUND OF THE INVENTION

This invention relates to new and useful compositions of matter classifiable in the field of organic chemistry as dibenzoxathiepins. More particularly, the instant invention relates to a novel group of 6H-dibenz[b,e][1,4]oxathiepins; to metnods of preparing such compounds; and to the method of employing them in the treatment and control of allergic conditions such as asthma.

SUMMARY OF THE INVENTION

In its composition aspect, therefore, the instant invention may be described as residing in the concept of isomeric 6H-dibenz[b,e][1,4]oxathiepins characterized by having the following structural formulae:

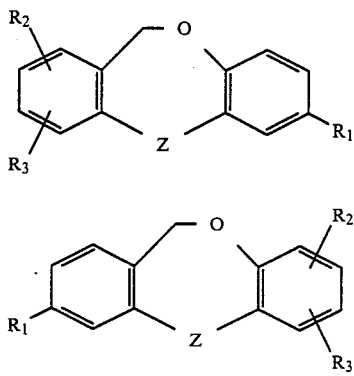

wherein Z is a member selected from the group consisting of thio, sulfinyl or sulfonyl; $R_2$ and $R_3$ are the same or different and are members selected from the group consisting of hydrogen, halogen, nitro, loweralkyl, amino, N-loweralkylamino, N,N-diloweralkylamino, loweralkanoyl, hydroxy, loweralkoxy, loweralkylthio, trifluoromethylthio, loweralkylsulfinyl, loweralkylsulfonyl or trifluoromethyl; and $R_1$ is a member selected from the group consisting of 5-tetrazolyl, 5-tetrazolylmethyl, 3-hydroxy-1,2,5-thiadiazol-4-yl, 4-hydroxy-$\Delta^3$-pyrroline-3-yl-2,5-dione or

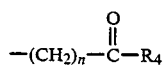

wherein n is an integer from 0-4 and $R_4$ is a member selected from the group consisting of hydroxy, loweralkoxy, N,N-diloweralkylaminoloweralkoxy, hydroxyloweralkoxy, arboxyloweralkoxy, amino, N-loweralkylamino, N,N-diloweralkylamino, loweralkylsulfonylamino, carboxyloweralkylamino, carboxamidoloweralkylamino, 2-imino-3-methylthiazolidine, loweracyloxyloweralkoxy or (5-methyl-2-oxo-1,3-dioxolan-4-yl)methoxy, and the pharmaceutically acceptable salts thereof.

DETAILED DESCRIPTION

As used herein, the term, halogen, includes chlorine, bromine, iodine and fluorine. The terms, loweralkyl and loweralkoxy, wherever employed, include straight and branched chain alkyl and alkoxy groups having 1 to 4 carbon atoms in the alkyl or alkoxy moiety such as, for example, methyl, ethyl, isopropyl, butyl, ethoxy, propoxy and isobutoxy. The term, loweralkanoyl, includes straight and branched chain alkanoyl groups of 1 to 4 carbon atoms including, for example, formyl, acetyl, propanoyl and butyryl.

The instant invention is based upon applicants' discovery that the oxathiepins of formula I and Ia, above, markedly antagonize the actions of contractile prostaglandins such as $PGF_{2\alpha}$, $PGG_2$, $PGH_2$ and $TXA_2$. The use of the oxathiepins of this invention, which act as prostaglandin antagonists, and biosynthesis inhibitors, offers a new approach to therapy in a variety of allergic conditions such as allergic asthma where excessive contractile activity of prostaglandins and prostaglandin biosynthetic intermediates occur. It is well known, for example, that prostaglandins such as $PGF_{2\alpha}$, $PGG_2$, $TXA_2$ and $PGH_2$ are potent contractants of bronchial muscle and that human asthmatics are especially sensitive to the bronchial constricting action of $PGF_{2\alpha}$. The antagonizing action of the oxathiepins of this invention against the constricting actions of contractile prostaglandins has been confirming in vitro and in vivo using standard pharmacological techniques. It is contemplated, therefore, that the oxathiepins of this invention will be employed in dosage unit form as the essential active ingredient in pharmaceutical formulations intended for the treatment and control of allergic conditions such as asthma in humans and warm blooded animals.

The novel oxathiepins of this invention, conveniently, are prepared from the 2-(or 9-)cyano intermediates having the following structural formulae:

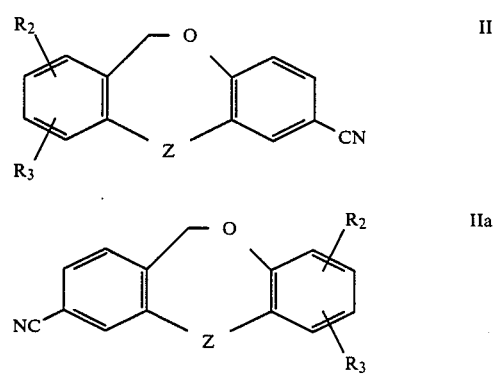

wherein $R_2$ and $R_3$ are as previously defined. These 2-(or 9-)cyano-6H-dibenz[b,e][1,4]oxathiepin intermediates are themselves readily prepared from well known starting materials which are either available commercially or may be prepared by conventional techniques already fully described in the chemical literature.

Thus, 2-cyano-6H-dibenz[b,e][1,4]oxathiepin (II) may be prepared according to the following general reaction scheme:

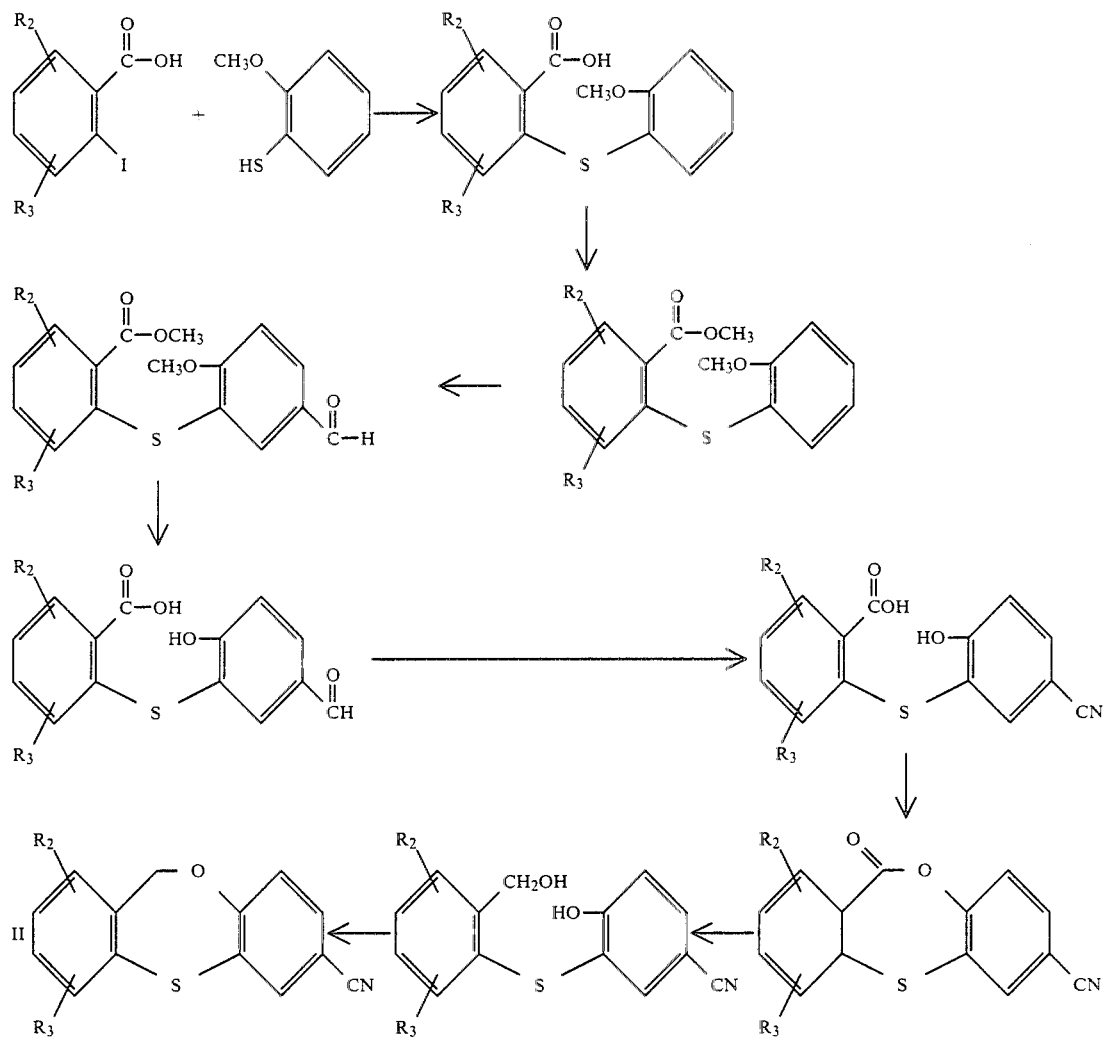

wherein $R_2$ and $R_3$ are as previously defined, by treating an appropriately substituted ($R_2$ and/or $R_3$) o-iodobenzoic acid with o-methoxythiophenol in the presence of copper powder and aqueous potassium hydroxide in order to obtain the corresponding 2-(o-methoxyphenylthio)benzoic acid. The reaction is carried out at reflux and usually requires 2 to 5 hours for completion. Upon recovery, the acid product may be converted into the corresponding lower alkanol ester by refluxing with a lower alkanol in the presence of a strong acid such as sulfuric acid, hydrochloric acid, trifluoroacetic acid and the like. The ester product then is treated with dichloromethyl methyl ether in the presence of titanium tetrachloride to form the corresponding 3-(o-carboloweralkoxyphenylthio)-4-methoxybenzaldehyde which then is demethylated with hydrogen bromide in glacial acetic acid to form the corresponding 3-(o-carboxyphenylthio)-4-hydroxybenzaldehyde. The aldehyde so produced then is treated with hydroxylamine hydrochloride in the presence of sodium formate and formic acid to form the corresponding 3-(o-carboxyphenylthio)-4-hydroxybenzonitrile which is treated with dichclohexylcarbodimide (DCC) to form the correpsonding 2-cyano-6H-6-oxo-dibenz[b,e][1,4]oxathiepin. The 2-cyano-oxatheipin product then is treated with an alkali metal borohydride to form the corresponding 3-(o-hydroxymethylphenylthio)-4-hydroxybenzonitrile which is reacted with dichclohexylcarbodiimide to form the desired 2-cyano-6H-dibenz[b,e][1,4oxthiepin of formula II.

9-Cyano-6H-dibenz[b,e][1,4]thiepin (IIa) may be prepared according to the following general reaction scheme:

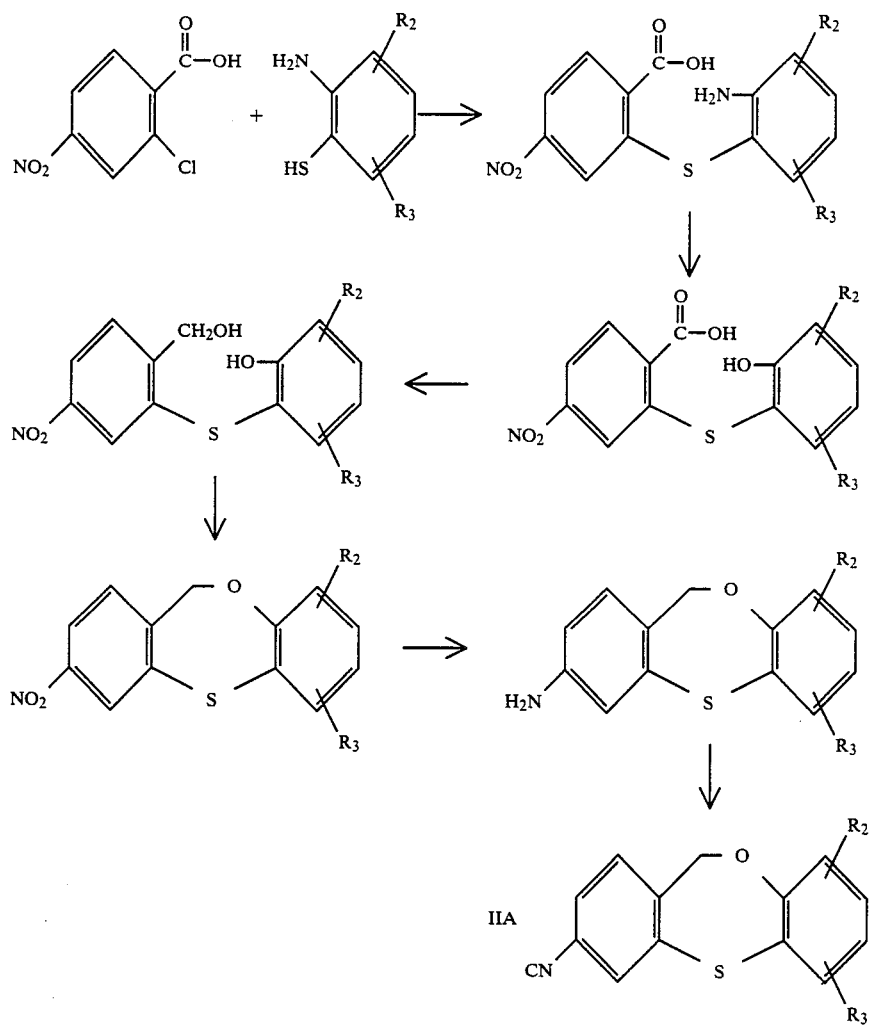

wherein $R_2$ and $R_3$ are as previously defined, by treating an appropriately substituted ($R_2$ and/or $R_3$) o-aminothiophenol with 2-chloro-4-nitrobenzoic acid in the presence of cuprous oxide to form the corresponding 2-(o-aminophenylthio)-4-nitrobenzoic acid which then is suspended in water, acidified with sulfuric acid, treated with sodium nitrite followed by sodium fluoroborate to obtain the diazonium fluoroborate which is heated in 50% sulfuric acid to obtain the corresponding 2-(o-hydroxyphenylthio)-4-nitrobenzoic acid. The acid product is treated with borane in tetrahydrofuran to form the corresponding 2-(o-hydroxyphenylthio)-4-nitrobenzyl alcohol which is cyclized in the presence of dicyclohexylcarbodiimide (DCC) to form the corresponding 9-nitro-6H-dibenz[b,e][1,4]oxathiepin. The nitro group then is reduced to the 9-amino compound with stannous chloride and the amine is treated with sodium nitrite followed by a mixture of cuprous cyanide and potassium cyanide to obtain the desired 9-cyano-6H-dibenz[b,e][1,4]oxathiepin of formula IIa.

The novel oxathiepins of the instant invention wherein the substituent at the 2-(or 9-)position is carboxy are prepared by refluxing the 2-(or 9-)cyano intermediates of formula II or IIa in a mixture of ethanol and aqueous sodium hydroxide. The reaction usually requires from 2 to 6 hours for completion and the desired 6H-dibenz[b,e][1,4]oxathiepin-2-(or 9-)carboxylic acid of formula III or IIIa is recovered from the reaction mixture upon acidification.

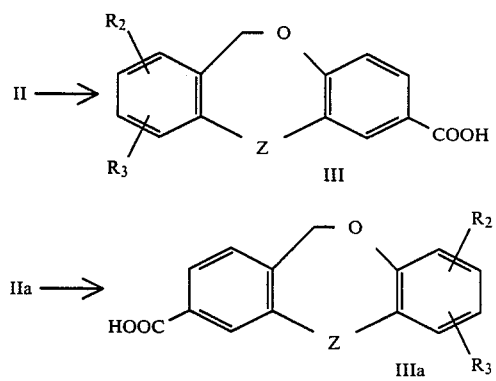

The novel oxathiepins of this invention wherein the substituent at the 2-(or 9-)position is 5-tetrazolyl also are prepared from the 2-(or 9-)cyano intermediates of formula II or IIa. The nitrile is heated in a mixture of sodium azide and ammonium chloride in a suitable organic solvent such as dimethylformamide. Conveniently, the reaction is carried out at reflux and usually requires 4 to 12 hours for completion. After dilution with excess sodium carbonate and extraction with ethyl acetate, the aqueous phase is acidified to obtain the desired 2-(or 9-)(1H-tetrazol-5-yl)-6H-dibenz[b,e][1,4]oxathiepin of formula IV or IVa.

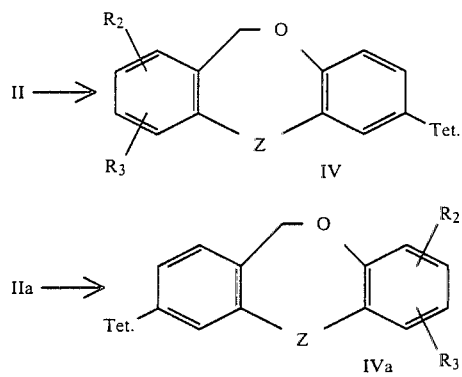

Formation of the 11-oxide or the 11,11-dioxide groups (e.g., preparation of the sulfinyl or sulfonyl compounds of the instant invention) conveniently is achieved by controlled oxidation techniques. Thus, for example, the carboxylic acid derivatives of formula III or IIIa may be oxidized with hydrogen peroxide in the presence of an acidic solvent such as acetic acid or with organic peroxides such as peroxy acids, for example, m-chloroperbenzoic acid and the like, in a stepwise fashion to form the corresponding sulfinyl derivative, formula V or Va, and sulfonyl derivative, formula VI or VIa, by controlling the molar ratio of oxidant to reductant. The molar ratio determines the oxidation level of the sulfur in the product. A 1:1 molar ratio, for example, results largely in the production of the sulfinyl derivative whereas a 2 to 3 molar excess of oxidant results in a yield predominately comprising the sulfonyl derivatives.

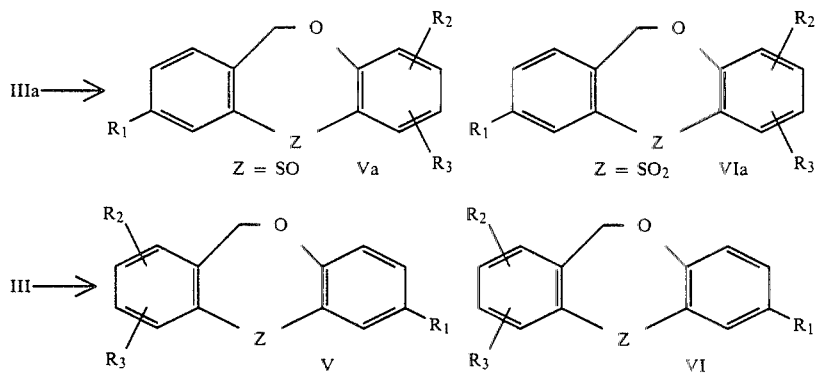

The oxidation technique described above is generally applicable to preparation of any of the sulfinyl or sulfonyl compounds of this invention from the corresponding oxathiepin. Thus, for example, the 5-tetrazolyl compounds of formula IV or IVa may be subjected to controlled oxidation in order to obtain the corresponding sulfinyl and sulfonyl compounds.

Alternatively, the 2-(or 9-)cyano intermediates of formula II or IIa may be oxidized as described above to produce the corresponding sulfinyl or sulfonyl intermediate. These intermediates then may be converted to the corresponding 2-(or 9-)carboxylic acid or 5-tetrazolyl compounds by the methods already described.

In addition to their therapeutic properties as noted above, the 2-(or 9-)carboxylic acid derivatives of this invention serve as valuable intermediates in the preparation of other variously substituted and therapeutically useful 6H-dibenz[b,e][1,4]oxathiepins of formula I and Ia. Thus, the 2-(or 9-)carboxylic acid of formula III or IIIa may be converted readily into the corresponding acid halide, preferably the acid chloride, by treating the carboxylic acid with a thionyl halide, preferably thionyl chloroide. The resulting 2-(or 9-)halocarbonyl-6H-dibenz[b,e][1,4]-oxathiepin (i.e., the 2-(or 9-)chlorocarbonyl compounds of formula VII or VIIa) then may be treated with various well-known reagents to form desired ester and amide derivatives.

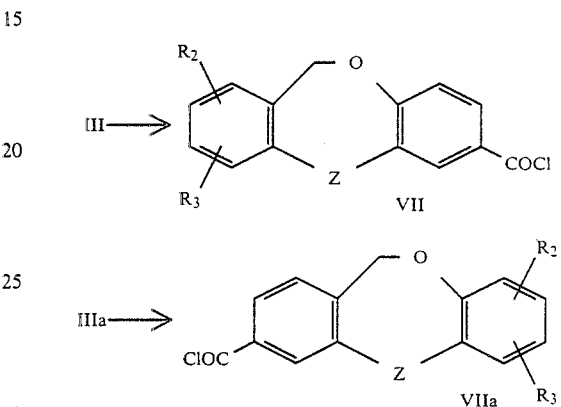

Thus, for example, the chlorocarbonyl compounds of formula VII and VIIa may be treated:

(a) with a loweralkano such as, for example, methanol, ethanol, 2-propanol, butanol and 2-butanol, to form the corresponding (R=) loweralkyl esters, VIII and VIIIa:

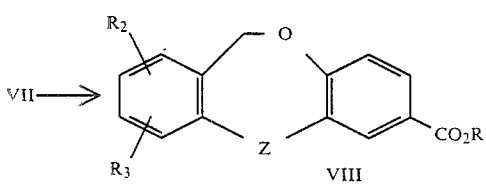

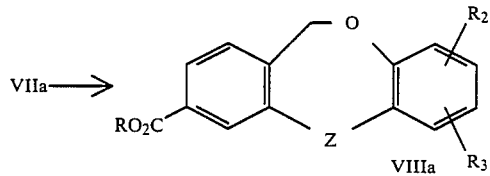

(b) with ammonia to form the corresponding carboxamides, X and IXa:

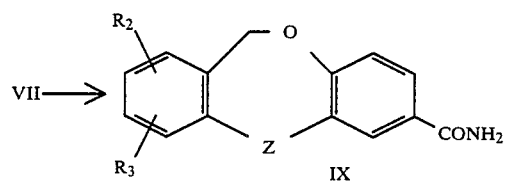

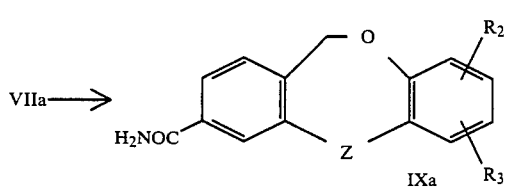

(c) with an N-loweralkylamine such as, for example, methylamine, ethylamine, propylamine, isopropylamine and butylamine, or an N,N-diloweralkylamine such as, for example, dimethylamine, diethylamine, dipropylamine and dibutylamine, to form the coresponding ($R_1=$) N-loweralkylcarboxammide X or Xa, or N,N-diloweralkylcarboxamide, XI or XIa:

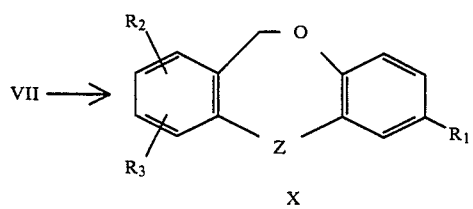

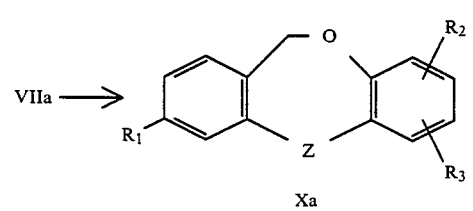

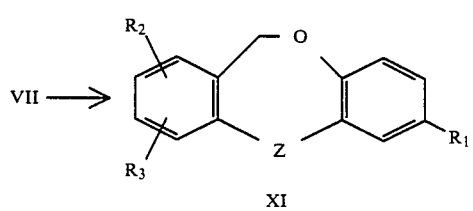

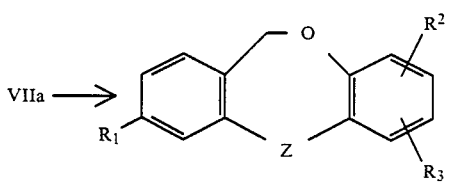

(d) with a loweralkylsulphonamide such as, for example, methanesulphonamide, ethanesulphonamide, propanesulphonamide and butanesulphonamide, to form the corresponding ($R_1=$) N-loweralkylsulfonylcarboxamide, XII or XIIa:

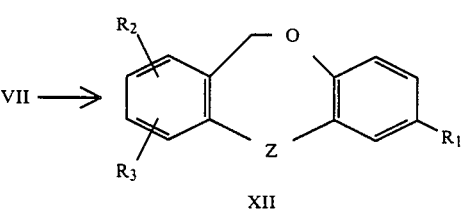

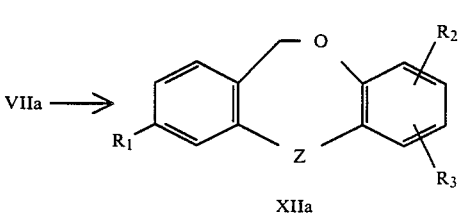

(e) with 2-imino-3-methylthiazollidine to form the corresponding ($R_1=$) (3-methyl-2-thiazolidinylidene) carboxmide, XIII and XIIIa:

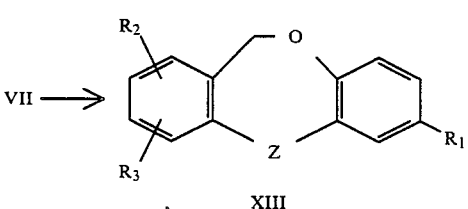

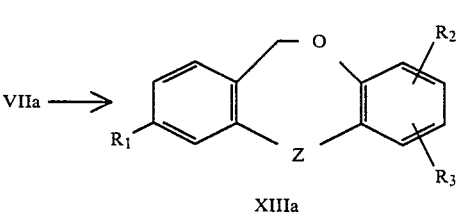

(f) with a loweralkyldiol such as, for example ethylene glycol, trimethylene glycol and 1,4-butanediol, to form the corresponding ($R_1=$) hydroxyloweralkylester, XIV and XIVa:

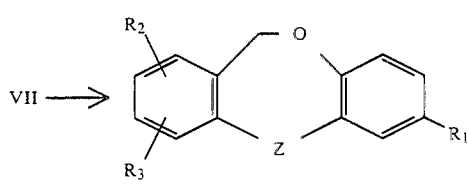

XIV

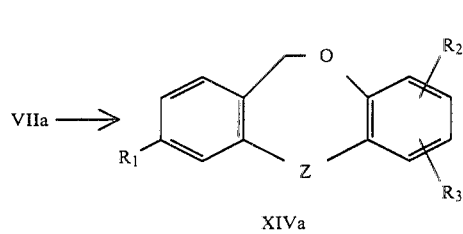

XIVa (g) with an N,N-diloweralkylaminoloweralkanol such as, for example, N,N-dimethylethanolamine, N,N-diethylethanolamine, 3-N,N-dimethylaminopropan-1-ol and 4-N,N-diethylaminobutan-1-ol, to form the corresponding ($R_1=$) N,N-diloweralkylaminoloweralkyl ester, XV and XVa:

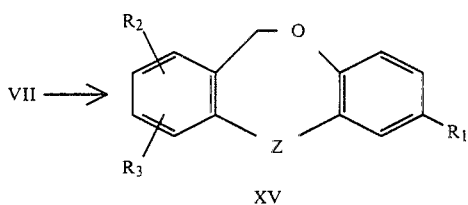

XV

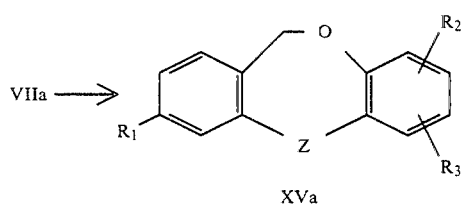

XVa (h) with an amino acid such as, for example, glycine, alanine and valine, to form the corresponding ($R_1=$) N-carboxyloweralkylcarboxamide, XVI and XVIa:

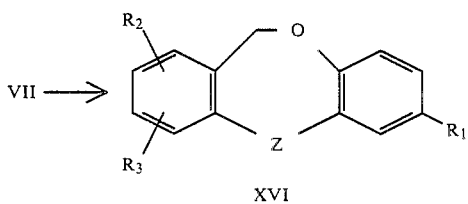

XVI

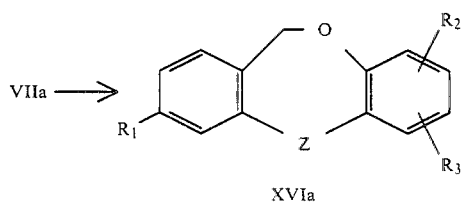

XVIa (i) with an alkali metal salt of a hydroxyloweralkanoic acid such as, for example, hydroxyacetic acid, 3-hydroxybutyric acid and β-hydroxypropionic acid, to form the corresponding ($R_1=$) Carboxyloweralkyl ester, XVII and XVIIa:

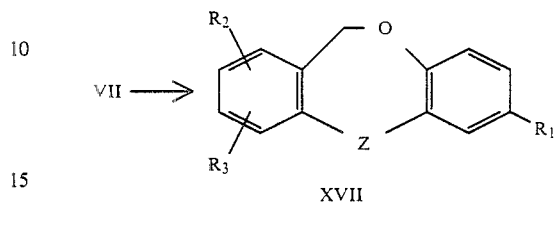

XVII

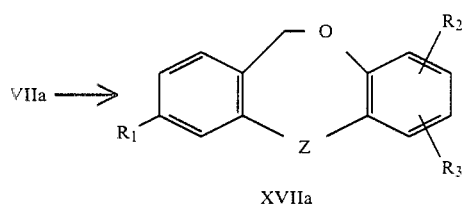

XVIIa

Where the corresponding sulfinyl or sulfonyl derivatives are desired, the corresponding 11-oxide or 11,11-dioxide 2-(or 9-)carboxylic acid, e.g. a compound of formula V, Va, VI or VIa, may be substituted for starting material III or IIIa in the foregoing reaction sequence. Alternatively, it will be clear to those skilled in the art that the product esters and amides obtained in the foregoing reaction sequence may be oxidized by the techniques already described to obtain the corresponding sulfinyl or sulfonyl derivatives.

Those oxathiepins of this invention wherein the substituent at the 2-(or 9-)position is 3-hydroxy-1,2,5-thiadiazol-4-yl are prepared by refluxing the 2-(or 9-)cyano intermediate in formic acid in the presence of Raney nickel alloy for 1 to 2 hours in order to obtain the corresponding 6H-dibenz[b,e][1,4]oxathiepin-2-(or 9-)carboxaldehyde. The aldehyde product then is converted into the corresponding 2-(or 9-)2-aminoacetonitrile by treatment with sodium cyanide in an alcoholic solvent saturated with ammonia and in the presence of ammonium chloride and ammonium hydroxide. The reaction usually is conducted at room temperature and requires from 8 to 16 hours to completion. The aminoacetonitrile so produced is treated with concentrated hydrochloric acid at room temperature for 20 to 45 minutes in order to obtain the corresponding 2-(or 9-)(2-aminoacetamide) which then is treated with sulfur monochloride in dimethylformamide to obtain the desired ($R_1=$) 2-(or 9-)(3-hydroxy-1,2,5-thiadiazol-4-yl) 6H-dibenz[b,e][1,4]oxathiepin of formula XVIII, XVIIIa. This reaction sequence is illustrated in the following diagram, it being understood that position of the 3-hydroxy-1,2,5-thiadiazol-4-yl substituent in the final product depends upon the selection of the appropriate 2-(or 9-)cyano starting material.

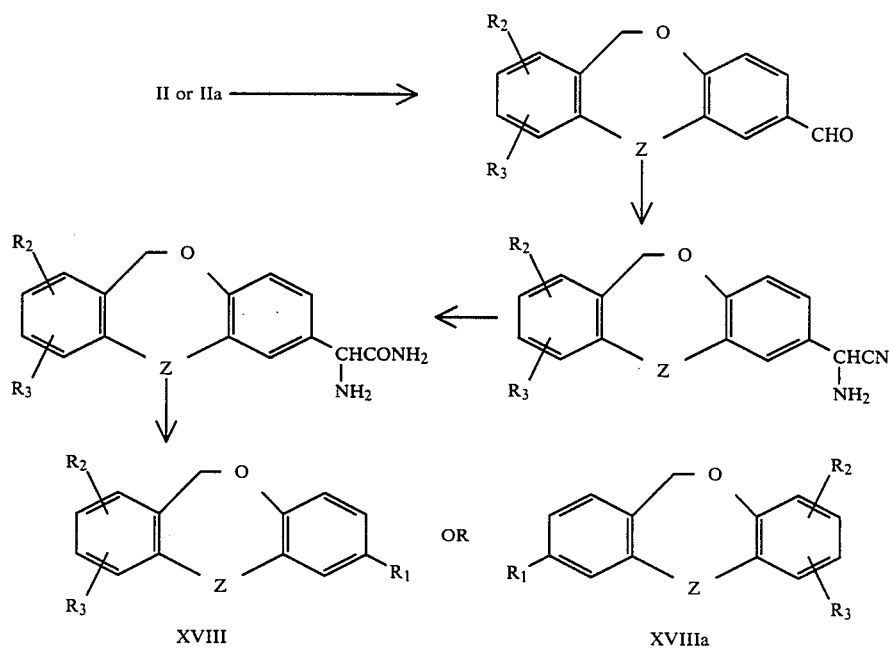

The novel oxathiepins of this derivative wherein the $R_1$ substituent at the 2-(or 9-) position is 4-hydroxy-$\Delta^3$-pyrroline-3-yl-2,5-dione are prepared from the appropriately substituted 2-(or 9-)carboxylic acid oy reducing the acid to the corresponding alcohol with borane in tetrahydrofuran. The reaction conveniently is carried out at room temperature under an inert atmosphere and usually requires 2 to 4 hours for completion. The alcohol then is brominated with phosphorous tribromide and the bromomethyl so produced is treated with sodium cyanide to form the corresponding 2-(or 9-)cyanomethyl derivative. These reactions may be carried out at room temperature and usually require from 1 to 3 hours for completion. The cyanomethyl intermediate then is hydrolyzed to the corresponding acetic acid which is treated with thionyl chloride followed by ammonia to form the corresponding 2-(or 9-)acetamide derivative by techniques already described. The acetamide then is treated with diethyl oxalate in dimethylformamide in the presence of potassium t-butoxide to form the desired ($R_1$=) 2-(or 9-)(4-hydroxy-$\Delta^3$-pyrrolin-3-yl-2,5-dione)-6H-dibenz[b,e][1,4]oxathiepin of formula XIX and XIXa.

This reaction sequence is illustrated in the diagram below, it again being understood that the position of the hydroxypyrrolinedione in the final product depends upon the selection of the 2-(or 9-) carboxylic acid starting material.

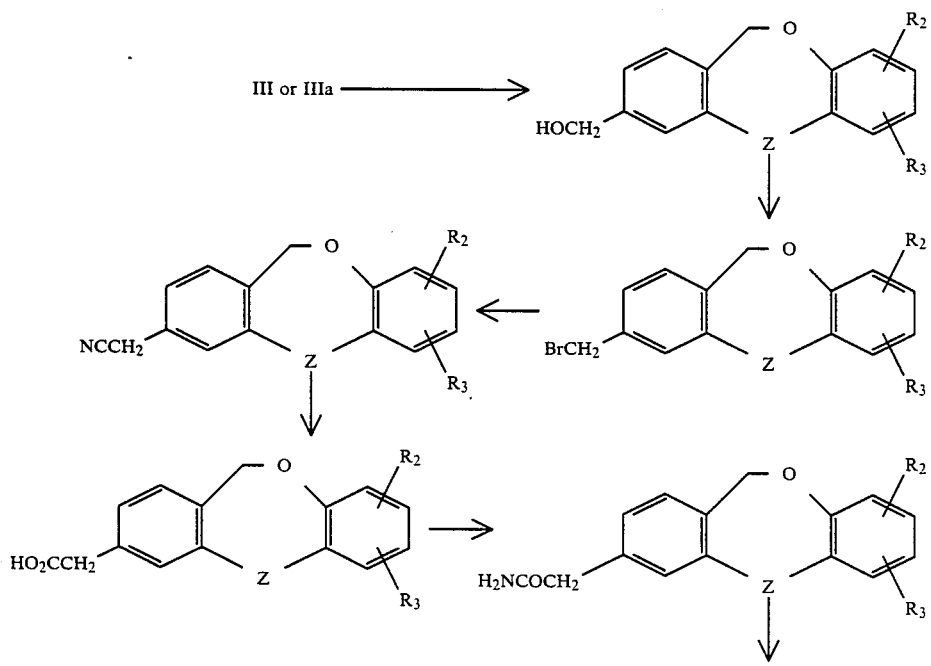

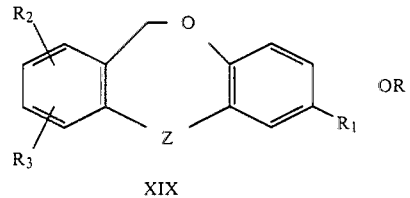   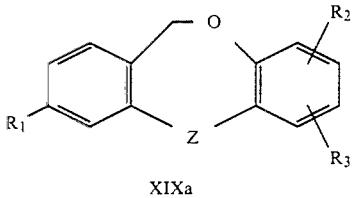

XIX                     XIXa

Where corresponding sulfinyl or sulfonyl derivatives are desired, the products of both reaction schemes described above may be oxdized by the techniques already described.

It will be noted that the reaction sequence described above afford as not only oxathiepins of this invention wherein the substituents at the 2-(or 9-) position is hydroxy-$\Delta^3$-pyrroline-3-yl-2,5-dione, but, in Steps A–D, lead also to the preparation of those oxathiepins of this invention wherein the substituent at the 2-(or 9-) position is a loweralkanoic acid (i.e., compounds of formula I and Ia, wherein $R_1$ is

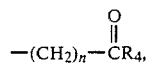
$-(CH_2)_n-CR_4$, n is an integer between 1 and 4 and $R_4$ is hydroxy). Thus, Steps A–D, as described above, starting with the appropriately substituted 2-(or 9-)carboxylic acid, through reduction, bromination, cyanization and oxidation afford the corresponding 2-(or 9-)acetic acid derivative. Quite obviously, the described reduction, bromination, cyanization and oxidation sequence can be repeated, employing the 2-(or 9-) acetic acid derivative as starting material, in order to obtain the corresponding propionic acid derivative which, in turn, can be employed as starting material for preparing the corresponding butyric acid derivative. In this manner, any desired 2-(or 9-) loweralkanoic acid derivative of the instant invention readily is prepared. Corresponding sulfinyl or sulfonyl derivatives are prepared by the oxidation techniques previously described.

The 2-(or 9-) cyano loweralkyl intermediates obtained from Steps A–C in the reaction sequence described above also serve as intermediates in the preparation of other therapeutically active oxathiepins of formula I or Ia. Thus, for example, an appropriately substituted 2-(or 9-) cyanomethyl-6H-dibenz[b,e][1,4]oxathiepin may be treated with sodium azide and ammonium chloride by techniques previously described to form the corresponding 2-(or 9-)(1H-tetrazol-5-yl-methyl)-6H-dibenz[b,e][1,4] oxanthiepin and the product, if desired, can be oxidized to form the corresponding sulfinyl or sulfonyl derivative.

The halogen substituted 6H-dibenz[b,e][1,4] thiepin derivatives ($R_2$ or $R_3$=F, Cl, Br or I) are prepared as shown in the following reaction sequence which illustrates the preparation of 8-(or 9-) fluoro-6H-dibenz[b,e][1,4]oxathiepin-2-carboxylic acid of formula XX and XXa and the corresponding -11,11-dioxide XXI and XXIa.

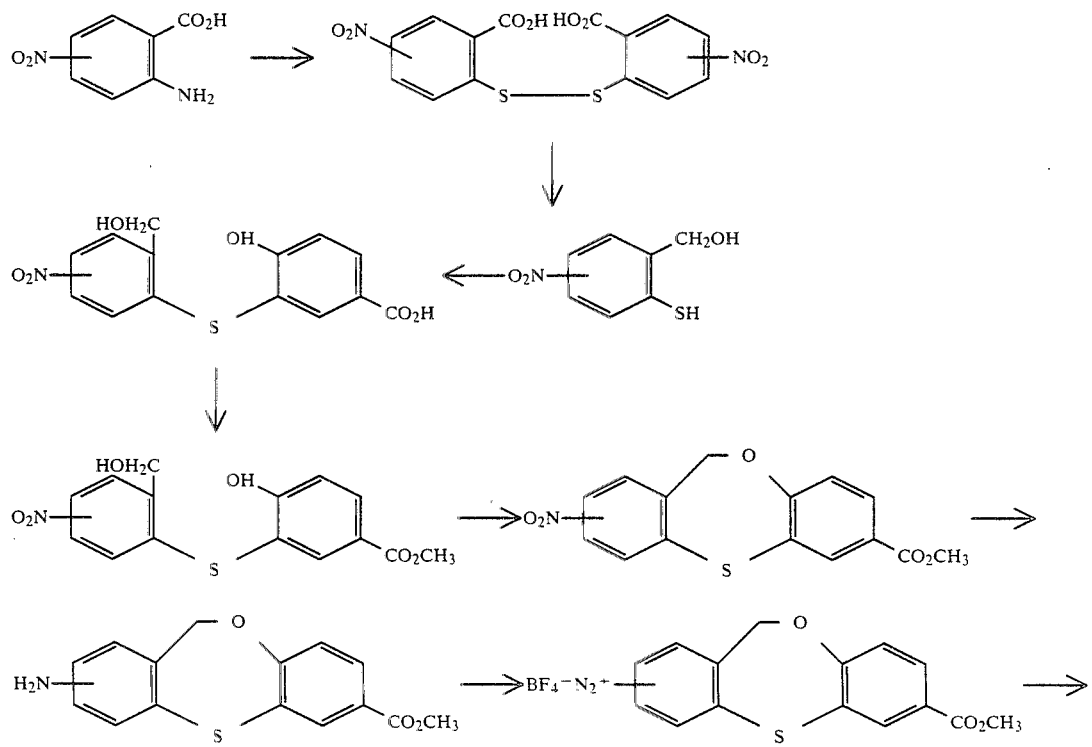

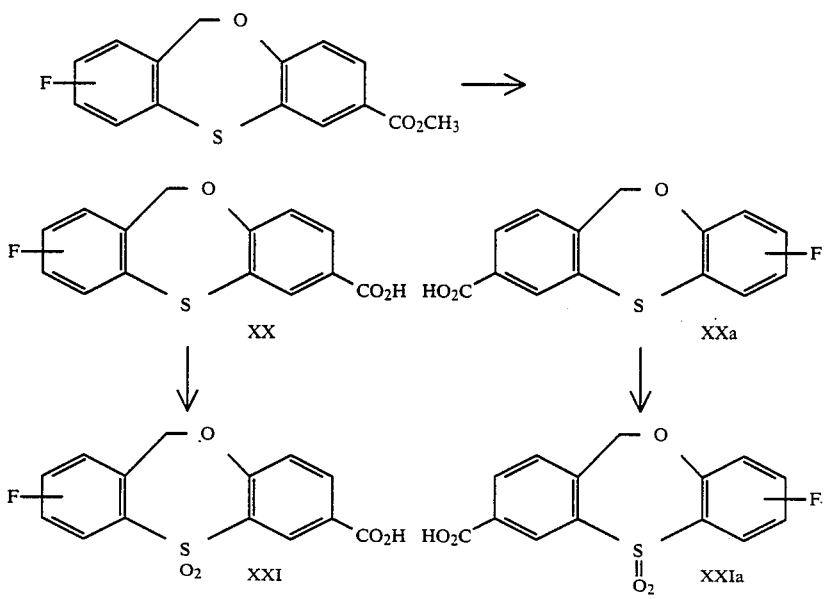

2-Amino-5-(or 4-) nitrobenzoic acid is converted into the disulfide carboxylic acid by reaction with (1) sodium nitrite and sulfuric acid; (2) potassium xanthogenate; and (3) sodium carbonate/water.

The disulfide is converted to 2-mercapto-5-(or 4-)nitrobenzyl alcohol by reductive cleavage using diborane.

Reaction of the mercaptonitrobenzyl alcohol with 4-hydroxy-3-iodo-benzoic acid in the presence of N-methyl-2-pyrrolidinone affords 3-(2-hydroxymethyl-4(or 5)-nitrophenylthio)-4-hydroxybenzoic acid.

Esterification of the benzoic acid is accomplished with methanol and sulfuric acid. Ring closure of the diol using diethyl azodicarboxylate and triphenylphosphine affords methyl 8- (or 9-) nitro-6H-dibenz[b,e][1,4]oxathiepin-2-carboxylate.

The 8-(or 9-) nitro group is then reduced using stannous chloride to afford the 8-(or 9-) amino compound. Reaction of the 8-(or 9-) amino compound with sodium nitrite and hydrogen tetrafluoroborate affords the diazonium tetrafluoroborate salt. Heating this salt affords the 8-(or 9-) fluoro compound.

Hydrolysis of the methyl 8-(or 9-) fluoro-6H-dibenz[b,e][1,4]oxathiepin-2-carboxylate with (1) sodium hydroxide/water; and (2) hydrochloric acid affords the 8-(or 9-) fluoro-6H-dibenz[b,e][1,4]oxathiepin- 2-carboxylic acid. Treatment of the carboxylic acid with hydrogen peroxide/acetic acid yields the compound 8- (or 9-) fluoro-6H-dibenz[b,e][1,4]oxathipin-2-carboxylic acid-11,11-dioxide.

As noted above, pharmaceutically acceptable salts of the novel oxathiepins also are included with the scope of this invention. The term, pharmaceutically acceptable salts, is intended to include salts derived from pharmaceutically acceptable non-toxic acids and bases such as, for example, ammonium salts, alkali metal salts such as sodium and potassium salts, alkaline earth metal salts such as magnesium and calcium salts, salts of organic bases such as amine salts derived from mono-, di- and triloweralkyl or hydroxyloweralkanyl amines such as trimethylamine, dimethylamine and triethanolamine, salts derived from heterocyclic amines such as piperidine, 1-methylpiperazine, piperazine and morpholine, and salts derived from pharmaceutically acceptable acids such as hydrochloric acid, sulfuric acid, tartaric acid and propionic acid.

It will be noted by the skilled artisan that many of the carboxylic acid derivatives encompassed by formulae I and Ia will serve as pro-drugs of the active carboxylate form in vivo. Several of these derivatives also possess bioactivity in their own right. For a general discussion of pro-drugs see A. A. Sinkula, *Ann. Rpts. Med. Chem.* 10 306–316 (1975), wherein the utility of pro-drug forms, for example esters, amides and amino acid amide derivatives of carboxylic acids are shown to provide useful means of administering the drug.

The oxathiepins of formula I and Ia are useful in the treatment and prophylaxis of human or warm-blooded animal disease conditions where excessive undesirable contractile activity of prostaglandins, such as $PGF_{2\alpha}$, or prostaglandin biosynthetic intermediates contribute. In particular, they are of value in the treatment and control of allergic conditions such as asthma.

The magnitude of a prophylactic or therapeutic dose of compound of formula I and Ia will, of course, vary with the nature and the severity of the condition to be treated and with the particular compound of formula I and Ia and its route of administration. In general, the dose range lies within the range of 0.2 mg to 100 mg per kg body weight per day.

The pharmaceutical compositions of the present invention comprise a compound of formula I and Ia as an active ingredient, and may also contain pharmaceutically acceptable carrier and optionally other therapeutic ingredients. The compositions include compositions suitable for oral, rectal, opthalmic, pulmonary, nasal, dermal, topical or parenteral (including subcutaneous, intramuscular and intravenous) administration, although the most suitable route in any given case will depend on the nature and severity of the condition being treated and on the nature of the active ingredient. They may be conveniently presented in unit dosage form and prepared by any of the methods well known in the art of pharmacy.

For use where a composition for intravenous administration is employed, a suitable dosage range is from 0.2 to 10 mg (preferably 1 to 8 mg) of a compound of formula I and Ia per kg of body weight per day and in the case where an oral composition is employed a suitable dosage range is about, e.g., 1 to 50 mg of a compound of formula I and Ia per kg of body weight per day, preferably from 5 to 40 mg/kg.

Pharmaceutical compositions of the present invention suitable for oral administration and by inhalation in the case of asthma therapy may be presented as discrete units such as capsules, cachets or tablets each containing a predetermined amount of the active ingredient; as a powder or granules; or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of powdered compound moistened with an inert liquid diluent. Desirably, each tablet contains from 50 mg to 500 mg of the active ingredient and each cachet or capsule contains from 50 mg to 500 mg of the active ingredient.

The best mode contemplated by applicants for carrying out their invention is illustrated in the following working examples. No limitation, however, is intended except as set forth in the appended claims.

EXAMPLE 1

9-Cyano-6H-dibenz[b,e][1,4]oxathiepin

Step A 2-(o-Aminophenylthio)-4-nitrobenzoic acid

Heat a mixture of 466 g (3.72 moles) of 2-aminothiophenol, 250 g (1.24 moles) of 2-chloro4-nitrobenzoic acid, 1.25 liters of quinoline, 192 g (1.34 moles) of cuprous oxide and 125 ml of pyridine in an oil bath at 160°–170° C. with mechanical stirring for 90 minutes. Cool the mixture to room temperature and add 1.87 liters of concentrated hydrochloric acid followed by 625 ml of water. Separate the precipitate and wash well with water. Extract the washed precipitate into boiling methanol and filter. Treat the hot filtrate with charcoal, filter and strip to dryness. Dissolve the residue in aqueous sodium hydroxide, filter and treat with charcoal. Acidify the filtrate and separate the precipitate. (Yield: 38 g).

Additional Crop: Take up the insoluble residue from the basic extraction into water, filter through Celite and acidify. Separate the precipitate and dissolve in ethyl acetate. Treat with charcoal, filter and strip to dryness. (Yield: 23 g).

Step B 2-(o-Hydroxyphenylthio)-4-nitrobenzoic acid

Suspend 10.15 g (35 mmoles) of the amino acid of Step A in 75 ml of water and add 4 ml concentrated sulfuric acid (7.36 g, 75 mmoles, 140 meq.). Cool the mixture in an ice-bath and add 3.657 g (53 mmoles) of sodium nitrite in portions at 0°–5° C. Stir the suspension in the cold for 20 minutes. Add 10 g (91 mmoles) of sodium fluoroborate and stir for an additional 20 minutes. Separate the precipitated crude diazonium fluoroborate, suspend the precipitate in 250 ml of 50% sulfuric acid and heat in an oil bath at 90°–100° C. for 45 minutes. Cool the mixture and separate the precipitate. (Yield: 7.76 g).

Step C 2-(o-Hydroxyphenylthio)-4-nitrobenzyl alcohol

Dissolve 42 g (0.144 mole) of the acid of Step B in 575 ml of tetrahydrofuran and add dropwise 275 ml of borane (0.275 mole $BH_3$) in tetrahydrofuran under a nitrogen atmosphere at room temperature. Stir at room temperature overnight. Slowly add excess water and concentrate to remove the tetrahydrofuran. Extract into ethyl acetate and add 120 g of silica gel to the ethyl acetate solution. Place the mixture atop a column of 1500 g of silica gel and elute with 20% ethyl acetate/benzene to obtain the pure diol. (m.p. 131°–133° C.).

Step D

9-Nitro-6H-dibenz[b,e][1,4]oxathiepin

Stir 4.5 g of the diol of Step C and 17.1 g (5 molar equivalents) of dicyclohexylcarbodiimide together at 110°–115° C. for 4–5 hours. Cool the mixture, dissolve in 250 ml of tetrahydrofuran and filter. Add silica gel to the filtrate and strip to dryness. Place the residue atop a column of 310 g of silica gel and elute with 50:50 benzene/hexane. Strip to dryness to obtain the title product. (m.p. 112°–113° C.).

Step E

9-Amino-6H-dibenz[b,e][1,4]oxathiepin

Dissolve 7.92 g of the nitro compound of Step D in 150 ml of tetrahydrofuran and add 50 ml of concentrated hydrochloric acid. Place the mixture in a cold water bath and add 22.7 g (3 molar equivalents + 10%) of stannous chloride dihydrate in portions. Stir at room temperature for 5½ hours. Dilute the reaction mixture with water, basify with 40% aqueous sodium hydroxide and extract with ethyl acetate. Wash the organics with water, dry and strip to dryness. (Yield: 7.22 g crude amine.)

Step F

9-Cyano-6H-dibenz[b,e][1,4]oxathiepin

Suspend 1.55 g (6.77 mmoles) of the amine of Step E in 36 ml of 1N hydrochloric acid and cool the mixture in an ice bath. Add slowly a solution of 502 mg (7.28 mmoles) of sodium nitrite in 10 ml of water, keeping the temperature at 0°–5° C. Stir the mixture in the cold for 15 minutes. Neutralize to pH 7 with aqueous sodium carbonate solution. Add the mixture slowly to a cooled mixture of 1.37 g (15.3 mmoles) of cuprous cyanide and 2.0 g (30.8 mmoles) of potassium cyanide in 50 ml of water at 0°–5° C. Recover the precipitate by filtration and wash well with water. Dissolve the precipitate in tetrahydrofuran, add silica gel and evaporate the tetrahydrofuran. Place the residue atop a silica gel column and elute with 50:50 benzene/hexane. Remove the solvent to obtain the title product. (m.p. 136°–137° C.).

EXAMPLE 2

9-Cyano-6H-dibenz[b,e][1,4]oxathiepin-11,11-dioxide

Dissolve 850 mg (3.56 mmole) of the 9-cyano-6H-dibenz[b,e][1,4]oxathiepin of Example 1 in 50 ml of methylene chloride. Add 2.3 g (11.3 mmole) of 85% m-chloroperbenzoic acid and stir at room temperature for 2 hours. Add excess calcium hydroxide and continue stirring for a few minutes. Filter the reaction mixture through celite and strip the filtrate to dryness. Chromatograph the residue on silica gel eluting with 25% ethyl acetate in benzene to obtain the title product. (m.p. 177°–179° C.).

EXAMPLE 3

6H-Dibenz[b,e][1,4]oxathiepin-9-carboxylic acid-11,11-dioxide

Reflux 435 mg of the nitrile of Example 2 in a mixture of 20 ml of 20% aqueous sodium hydroxide and 20 ml of ethanol for 2½ hours and cool to room temperature. Dilute the reaction mixture with water and remove most of the ethanol by evaporation under reduced pressure. Extract the aqueous residue with ethyl acetate. Acidify the aqueous solution, after evaporation of residual ethyl acetate, and separate the precipitate by filtration to obtain the title product. (m.p. 262°–265° C.).

EXAMPLE 4

9-(1H-Tetrazol-5-yl)-6H-dibenz[b,e][1,4]oxathiepin-11,11-dioxide

Heat together 435 mg (1.61 mmole) of the nitrile of Example 2, 156 mg (2.4 mmole) of sodium azide and 161 mg (3 mmole) of ammonium chloride in 10 ml of dimethylformamide at 135° C. for 6 hours. Cool the reaction mixture to room temperature, dilute with water and excess aqueous sodium carbonate solution and extract with ethyl acetate. Acidify and extract the separated solid with ethyl acetate or triturate in ether. Filter and dissolve the product in 40 ml of hot methanol. Filter and concentrate the filtrate to 15 ml. Cool and scratch to induce crystallization. Dry under vacuum at 130° C. to obtain the title product. (m.p. dec. 225° C.).

EXAMPLE 5

6H-Dibenzo[b,e][1,4]oxathiepin-9-carboxylic acid

Reflux 800 mg of the nitrile of Example 1 in a mixture of 25 ml of 20% sodium hydroxide and 25 ml of ethanol for 3 hours. Cool the reaction mixture to room temperature and remove most of the ethanol by evaporation under reduced pressure. Dissolve the precipitated sodium salt by diluting with water and warming. Extract with ethyl acetate and acidify the aqueous phase. Separate the precipitate by filtration to obtain the title product. (m.p. 241°–243° C.).

EXAMPLE 6

6H-Dibenz[b,e][1,4]oxathiepin-9-carboxylic acid-11-oxide

Dissolve with warming 380 mg of the carboxylic acid of Example 5 in 38 ml of glacial acetic acid. Place the reaction mixture in an oil bath at 40° C. and, after equilibration, add 1.5 ml of 30% hydrogen peroxide. Stir the mixture at 40° C. for 3½ hours until solution clears. Dilute with 300 ml of water and separate the precipitate by filtration to obtain the title product (m.p. 242°–245° C.).

EXAMPLE 7

9-(1H-Tetrazol-5-yl)-6H-dibenz[b,e][1,4]oxathiepin

Heat a mixture of 800 mg (3.35 mmole) of the nitrile of Example 1, 293 mg (4.5 mmole) of sodium azide and 265 mg (4.95 mmole) of ammonium chloride in 25 ml of dimethylformamide at 130°–135° C. for 6 hours. Dilute the mixture with water and excess sodium carbonate. Extract with ethyl acetate. Acidify the aqueous phase and separate the precipitate by filtration to obtain the title product. (m.p. melts with dec. 195°–200° C.).

EXAMPLE 8

9-(1H-Tetrazol-5-yl)-6H-dibenz[b,e][1,4]oxathiepin-11-oxide

Dissolve with warming 500 mg (1.77 mmole) of the tetrazolyl compound of Example 7 in 50 ml of glacial acetic acid. Place the reaction mixture in an oil bath at 45° C. and, after equilibration, add 2 ml of 30% hydrogen peroxide. Stir at 45° C. for several hours until the sulfoxide crystallizes out. (m.p. dec. 292°–295° C.).

EXAMPLE 9

2-Cyano-6H-dibenz[b,e][1,4]oxathiepin

Step A 2-(o-Methoxyphenylthio) benzoic acid

Stir under reflux for 3 hours a mixture of 70 g (0.5 mole) of o-methoxythiophenol, 120.5 g (0.486 mole) of o-iodobenzoic acid 81.7 g (1.46 mole) of potassium hydroxide, 85 g (1.34 mole) of copper powder and 800 ml of water. Filter the reaction mixture hot and again filter the filtrate through celite. Acidify the filtrate with concentrated hydrochloric acid. Separate the precipitate, wash well with water and dry in vacuo at 70° C. to obtain the title product. (m.p. 198°–200° C.)

Step B

Methyl 2-(o-methoxyphenylthio)benzoate

Dissolve 115 g of the acid of Step A in 3.5 liters of methanol and add slowly 25 ml of sulfuric acid. Stir under reflux for 72 hours. Cool the reaction mixture to room temperature and add 100 g of sodium bicarbonate in portions. Stir for an additional hour and strip to dryness. Dissolve the residue in methylene chloride and wash the solution three times with water. Dry the solution and strip to an oil which solidifies. (m.p. 82°–84° C.)

Step C 3-(o-Carbomethoxypheylthio-)4-methoxybenzaldehyde

Dissolve 117 g (0.427 mole) of the ester of Step B in 1500 ml of 1,2-dichloroethane and cool with stirring in an ice-bath. Add 200 ml (345 g, 1.82 mole) of titanium tetrachloride at a rapid dropwise rate. Add also fairly rapidly 154 g (1.34 mole) of dichloromethyl methyl ether. Stir the mixture under a nitrogen atmosphere overnight then pour into ice. After shaking, separate the organic phase and extract the aqueous phase twice with methylene chloride. Wash the combined organic phases twice with water, dry and strip to an oil which crystallizes. (m.p. 99°–104° C.).

Step D 3-(o-Carboxyphenylthio)-4-hydroxybenzaldehyde

Heat 126 g of the aldehyde of Step C in a mixture of 1500 ml of glacial acetic acid and 1500 ml of 48% hydrogen bromide in an oil bath at 150° C. with mechanical stirring until no trace of nondemethylated product remains (4–5 days). Col the reaction mixture and pour into 7 liters of water. Separate the precipitate, wash well with water and dry in vacuo at 70° C. to constant weight. (Yield: 108.2 g).

Step E 3-(o-Carboxyphenylthio)-4-hydroxybenzonitrile

Reflux 91.3 g of the aldehyde of Step D, 27.4 g of hydroxylamine hydrochloride and 41.9 g of sodium formate in 900 ml of formic acid (98–100%) for 1¼ hours. Cool the mixture and pour into 2½ liters of cold water. Separate the precipitate, wash with water and dry in vacuo at 75° C. (Yield: 82 g).

Step F

2-Cyano-6H-6-oxo-dibenzo[b,e][1,4]oxathiepin

Stir together at room temperature overnight 8.4 g of the nitrile of Step E and 19.16 g (3 molar equivalents) of dicyclohexylcarbodiimide in 400 ml of ethyl acetate. Filter the reaction mixture to remove the urea. Strip the filtrate to dryness. Triturate the residue in a small volume of ethyl acetate and filter. (Yield 5.5 g purple solid).

Strip the filtrate to dryness and chromatograph on a column of silica gel, eluting with benzene. (Yield 2.1 g white solid), (yield total: 7.6 g).

Step G 3-(o-Hydroxymethylphenylthio-)4-hydroxybenzonitrile

Dissolve 31.25 g (0.123 mole) of the nitrile of Step F in 750 ml of tetrahydrofuran and add 10.4 g (0.274 moles) of sodium borohydride. Stir the solution at room temperature for 1½ hours. Add water in small portions until foaming ceases. Remove the tetrahydrofuran by evaporation. Shake the residue with ethyl acetate, water and dilute hydrochloric acid. Separate the organic phase and extract the aqueous phase three times with ethyl acetate. Wash the combined organic phases with two small volumes of water, dry and strip to a thick oil which solidifies. (Yield: 39 g).

Step H

2-Cyano-6H-dibenz[b,e][1,4]oxathiepin

Stir the crude nitrile of Step F (assumed 100% yield, 0.123 mole) and 38 g (50% excess) of dicyclohexylcarbodiimide at 105°–110° C. for 1½ hours. Cool the reaction mixture and extract with methylene chloride. Filter to remove the dicyclohexylurea and strip the filtrate to dryness. Triturate in a small volume of ethyl acetate, filter and strip to dryness. Extract four times with hot benzene and strip the combined extracts to dryness. Chromatograph on a silica gel column, eluting with benzene to obtain the title product. (m.p. 145°–147° C.).

EXAMPLE 10

6H-Dibenzo[b,e][1,4]oxathiepin-2-carboxylic acid

Reflux 3.2 g of the nitrile of Example 9 for 5 hours in a mixture of 50 ml of 20% sodium hydroxide and 50 ml of ethanol. Allow the resulting clear solution to stand at room temperature overnight. Evaporate the ethanol. Dilute the residue with 200 ml of water and heat on a steam bath to dissolve. Filter and acidify the filtrate. Separate the precipitate, wash and dry in vacuo at 75° C. to obtain the title product. (m.p. 225°–227° C.).

EXAMPLE 11

6H-Dibenz[b,e][1,4]oxathiepin-2-carboxylic acid 11-oxide

Suspend 2 g of the acid of Example 10 in 70 ml of acetic acid and add 7 ml of 30% hydrogen peroxide. Heat at 55° C. for 2½ hours. Cool the reaction mixture to room temperature. Separate the precipitate, wash with acetic acid and dry. Dissolve the product in 150 ml of boiling tetrahydrofuran and filter. Concentrate the filtrate to 50 ml. Cool and separate the precipitate to obtain the title product. (m.p. 284°–286° C. slow dec.).

EXAMPLE 12

6H-Dibenz[b,e][1,4]oxathiepin-2-carboxylic acid-11,11-dioxide

Suspend 1.3 g of the acid of Example 10 in 50 ml of glacial acetic acic and add 7 ml of 30% hydrogen peroxide. Heat slowly to 75° C. and stir for 5 hours. Allow the reaction mixture to stand at room temperature overnight. Separate the precipitate, wash with acetic acid and dry to obtain the title product. (m.p. 279°–282° C.).

EXAMPLE 13

2-(1H-Tetrazol-5-yl)-6H-dibenz[b,e][1,4]oxathiepin

Reflux 3 g (12.55 mmole) of the nitrile of Example 9, 1 g (15.4 mmole) of sodium azide and 1 g (18.7 mmole) of ammonium chloride in 40 ml of dimethylformamide overnight. Cool to room temperature. Add aqueous sodium bicarbonate and ethyl acetate and stir the mixture for 30 minutes. Separate the aqueous phase and extract with ethyl acetate. Acidify the aqueous phase and separate the title product by filtration. (m.p. 230° C. dec.).

EXAMPLE 14

2-(1H-Tetrazol-5-yl)-6H-dibenz[b,e][1,4]oxathiepin-11-oxide

Suspend 2 g of the tetrazolyl compound of Example 13 in 120 ml of acetic acid. Add 15 ml of 30% hydrogen peroxide. Place the reaction mixture in an oil bath and heat slowly to 60° C. Stir at 60° C. for 2 hours. Cool to room temperature, filter, wash the precipitate with acetic acid and dry to obtain the title product. (m.p. 282° C. dec.).

EXAMPLE 15

2-(1H-Tetrazol-5-yl)-6H-dibenz[b,e][1,4]oxathiepin-11,11-dioxide

Suspend 600 mg of the tetrazole compound of Example 13 in 40 ml of glacial acetic acid and add 5 ml of 30% hydrogen peroxide. Heat to 70°–75° C. for 2½ hours until a clear solution is obtained. Cool the reaction mixture to room temperature. Separate the precipitated title product, wash with acetic acid and air dry. (m.p. 255° C. dec.).

EXAMPLE 16

Methyl 6H-dibenz[b,e][1,4]oxathiepin-9-carboxylate

Step A

9-Chlorocarbonyl-6H-dibenz[b,e][1,4]oxathiepin

Dissolve 5.16 g of 6H-dibenz[b,e][1,4]oxathiepin-9-carboxylic acid in 100 ml of chloroform and 50 ml of thionyl chloride and add to the mixture 1.0 ml of dimethylformamide. Allow the mixture to stand at room temperature for 72 hours. Evaporate the mixture to dryness to obtain the desired acid chloride.

Step B

Methyl 6H-dibenz[b,e][1,4]oxathiepin-9-carboxylate

Dissolve 2.0 g of the acid chloride of Step A in 20 ml of tetrahydrofuran containing 1.0 ml of methanol and 4 ml of pyridine. Allow the mixture to stand at room temperature for 24 hours then evaporate to dryness. Dissolve the residue in 1:4 ether/hexane and filter through silica gel. Evaporate the filtrate to dryness to obtain the title product.

Employing the process of Example 16, but substituting another lower alkanol such as, for example, ethanol, 2-propanol, butanol or 2-butanol, for the methanol of Step B, the corresponding lower alkyl esters of 6H-dibenz[b,e][1,4]-oxathiepin-9-carboxylic acid are obtained.

EXAMPLE 17

Methyl 6H-dibenz[b,e][1,4]oxathiepin-2-carboxylate

Repeat the process of Example 16, substituting 6H-dibenz[b,e][1,4]oxathiepin-2-carboxylic acid for the 6H-dibenz[b,e][1,4]oxathiepin-9-carboxylic acid of Step A, in order to obtain the title product. By substituting, where desired, other lower alkanols such as, for example, ethanol, 2-propanol, butanol or 2-butanol, for the methanol of Step B, the corresponding lower alkyl esters of 6H-dibenz[b,e][1,4]oxathiepin-2-carboxylic acid are obtained.

EXAMPLE 18

6H-Dibenzo[b,e]1,4]oxathiepin-2-carboxamide

Step A

2-Chlorocarbonyl-6H-dibenz[b,e][1,4]oxathiepin

Heat a solution of 5 g of 6H-dibenz[b,e][1,4]oxathiepin-2-carboxylic acid and 40 ml of thionyl chloride under reflux for 20 minutes. Evaporate the reaction mixture under vacuum to dryness. Repeat the evaporation with two 30 ml portions of carbon tetrachloride. Crystallize the residue from diisopropyl ether to obtain the title product.

Step B

6H-Dibenzo[b,e][1,4]oxathiepin-2-carboxamide

Dissolve the acid chloride from Step A in 20 ml of dry tetrahydrofuran and add this solution dropwise with stirring to a cooled (ice-bath) saturated solution of ammonia in 60 ml of tetrahydrofuran. Pass ammonia through the reaction mixture continuously for 15 minutes. Stir at room temperature for an additional 15 minutes and evaporate the reaction mixture to dryness. Add a mixture of 12 ml of ethanol and 60 ml of water to the residue and stir at room temperature for an additional 30 minutes. Separate the solid by filtration and wash with water, then with ethanol and then with ether. Dry in vacuo to obtain the title product.

In a similar manner, substituting 6H-dibenz[b,e][1,4]oxathiepin-9-carboxylic acid for the 6H-dibenz[b,e][1,4]oxathiepin-2-carboxylic acid in Step A, there is obtained 6H-dibenz[b,e][1,4]oxathiepin-9-carboxamide.

EXAMPLE 19

6H-Dibenzo[b,e][1,4]oxathiepin-2-N-methylcarboxamide

Add 6.0 g of 2-chlorocarbonyl-6H-dibenz[b,e][1,4]oxathiepin to 4 g of methylamine in 100 ml of methylene chloride at 0°–5° C. Add 13 ml of triethylamine dropwise over 10 minutes then stir the reaction mixture at room temperature overnight. Extract the reaction mixture with water, dry the organic layer and evaporate to dryness. Chromatograph over silica gel eluting with 200:20 toluene/dioxane. Evaporate eluate to dryness and recrystallize residue from methanol to obtain the title product.

In a similar manner, substituting another N-loweralkylamine such as, for example, ethylamine, propylamine, isopropylamine, butylamine and the like, or a N,N-diloweralkylamine such as, for example, dimethylamine, diethylamine, dipropylamine, dibutylamine and the like, for the methylamine employed above, there is obtained the corresponding 6H-dibenz [b,e][1,4]oxathiepin-2-N-loweralkylcarboxamide or 2-N,N-di-loweralkylcarboxamide. Corresponding 6H-dibenz[b,e][1,4]oxathiepin-9-N-loweralkylcarboxamides and 9-N,N-di-loweralkylcarboxamides are prepared by substituting 9-chlorocarbonyl-6H-dibenz[b,e][1,4]oxathiepin for the 2-chlorocarbonyl-6H-dibenz[b,e][1,4]oxathiepin employed above.

Also in a similar manner, substituting a carboxyloweralkylamine such as, for example, glycine, valine, leucine, isoleucine and the like, or the N-loweralkyl derivatives thereof, such as for example, N-methylglycine, N-propyleucine, N-butylisoleucine and the like, there is obtained the corresponding 6H-dibenz[b,e][1,4]oxathiepin-9-(or 2-)carboxyloweralkylcarboxamides or the N-loweralkyl derivatives thereof.

EXAMPLE 20

6H-Dibenz[b,e][1,4]oxathiepin-2-N-methanesulfonylcarboxamide

Heat 5.0 g of 6H-dibenz[b,e][1,4]oxathiepin-2-carboxylic acid in 50 ml of thionyl chloride for 15 minutes at reflux and then distill off the excess thionyl chloride. Evaporate the residue twice with small volumes of benzene. Add the resulting acid chloride to 4.0 g of methanesulphonamide in 100 ml of methylene chloride at 0°–5° C. Add dropwise over 10 minutes 15 ml of triethylamine. Stir the mixture at room temperature overnight. Extract the reaction mixture with 100 ml of 0.5N sodium hydroxide, wash the alkaline extract with ether and acidify with 6N hydrochloric acid. Separate the solids by filtration and dry in vacuo over potassium hydroxide. Chromatograph over silica gel eluting with 200:20:3 toluene/dioxane/acetic acid. Evaporate the eluate to dryness and recrystallize the residue from methanol to obtain the title product.

In a similar manner, substituting another loweralkylsulphonamide such as, for example, ethanesulphonamide, propanesulphonamide, butanesulphonamide and the like, for the methanesulphonamide employed above, there is obtained the corresponding 6H-dibenz[b,e][1,-

4]oxathiepin-2-N-loweralkylsulfonylcarboxamide. Corresponding 6H-dibenz[b,e][1,4]oxathiepin-9-N-loweralkylsulfonylcarboxamides are prepared by substituting 6H-dibenz[b,e][1,4]-oxathiepin-9-carboxylic acid for the 6H-dibenz[b,e][1,4]oxathiepin-2-carboxylic acid employed above.

EXAMPLE 21

6H-Dibenz[b,e][1,4]oxathiepin-2-(3-methyl-2-thiazolidinylidene)carboxamide

Reflux 1.0 g of 6H-dibenz[b,e][1,4]oxathiepin-2-carboxylic acid in 15 ml of thionyl chloride for 30 minutes. Strip the reaction mixture to dryness and dissolve the residue in 25 ml of methylene chloride. Add a solution of 1.0 g of 2-imino-3-methylthiazolidine in 10. ml of methylene chloride. Stir at room temperature for 30 minutes and add water. Continue stirring for 10 minutes. Separate the organic phase and wash with water and dry overnight over sodium sulfate. Strip to dryness. Stir and triturate the residue in ether, then in methanol. Chromatograph the resulting solid over silica gel, eluting with 20% ethylacetate in benzene. Strip to dryness to obtain the title product.

EXAMPLE 22

2-(3-Hydroxy-1,2,5-thiadiazol-4-yl)-6H-dibenz[b,e][1,4]oxathiepin

Step A

6H-Dibenz[b,e][1,4]oxathiepin-2-carboxaldehyde

Heat a mixture of 5.0 g of 2-cyano-6H-dibenz[b,e][1,4]oxathiepin and 4.0 g of Raney nickel alloy in 60 ml of 75% (v/v) aqueous formic acid at reflux for 1.5 hours. Cool to room temperature and filter. Concentrate to small volume and extract with methylene chloride. Wash the extract with water and with 1N sodium bicarbonate until neutral. Dry the neutral extract over sodium sulfate and concentrate to dryness to obtain the title product.

Step B

6H-Dibenz[b,e][1,4]oxathiepin-2-(2-aminoacetonitrile)

Stir at room temperature for 12 hours a mixture of 5.85 g of ammonium chloride, 5.3 g of sodium cyanide 75 ml of ammonium hydroxide, 100 ml of ethanol saturated with ammonia and 12 g of the carboxaldehyde of Step A. Pour the reaction mixture into 300 ml of water and extract with ether. Dry the extract over sodium sulfate and concentrate to dryness to obtain the title product.

Step C

6H-Dibenz[b,e][1,4]oxathiepin-2-(2-aminoacetamide)

Stir at room temperature 5.0 g of the aminoacetonitrile of Step B in 30 ml of concentrated hydrochloric acid for 30 minutes. Slowly pour the reaction mixture into cold ammonium hydroxide. Extract the mixture with ether and dry over sodium sulfate. Evaporate the extract to dryness to obtain the title product.

Step D 2-(3-Hydroxy-1,2,5-thiadiazol-4-yl)-6H-dibenz[b,e][1,4]oxathiepin

Stir overnight at room temperature a mixture of 1.365 g of the aminoacetamide of Step C, 1.989 g of sulfur monochloride and 5 ml of dimethylformamide. Filter the reaction mixture and then partition between ice-water (75 ml) and ethyl acetate (75 ml). Filter, separate the organic layer, wash with saturated aqueous sodium chloride solution and dry over magnesrum sulfate. Evaporate to dryness and dissolve the residue in 200 ml of boiling ethanol, treat with charcoal and filter. Concentrate to 25 ml, and separate the solids by filtration to obtain the title proouct.

By substituting 9-cyano-6H-dibenz[b,e][1,4]oxathiepin for the 2-cyano-6H-dibenz[b,e][1,4]oxathiepin employed in Step A above, there is obtained the corresponding 9-(3-hydroxy-1,2,5-thiadiazol-4-yl)-6H-dibenz[b,e][1,4]oxathiepin.

EXAMPLE 23

2-(4-Hydroxy-$\Delta^3$-pyrrolin-3-yl-2,5-dione)-6H-dibenz[b,e][1,4]oxathiepin

Step A

2-Hydroxymethyl-6H-dibenz[b,e][1,4]oxathiepin

Dissolve 5.1 g of 6H-dibenz[b,e][1,4]oxathiepin-2-carboxylic acid in 100 ml of tetrahydrofuran and add 35 ml of 1M borane in tetrahydrofuran at room temperature under a nitrogen atmosphere. Stir the mixture at room temperature for 3 hours. Slowly dilute the reaction mixture with water and then with ethyl acetate. Wash with aqueous sodium chloride, dry and evaporate to an oil. Yield 4.93 g (crude).

Step B

2-Bromomethyl-6H-dibenz[b,e][1,4]oxathiepin

Dissolve 4.43 g of the crude alcohol of Step A in 100 ml of benzene and add 1 ml (10.5 mmole) of phosphorous tribromide. Stir at room temperature for 1 hour, add water and then dilute with toluene. Wash three times with water, dry and strip to a solid residue. (Yield, 6.9 g, holding toluene)

Step C

2-Cyanomethyl-6H-dibenz[b,e][1,4]oxathiepin

Dissolve 6.4 g of the bromide of step in 75 ml of dimethylformamide and add 2.95 g of sodium cyanide. Stir the mixture at room temperature for 1.5 hours. Dilute with 600 ml of water and extract three times with ether. Wash the combined organics with water, dry and strip to a solid residue. Triturate in hexane and recover the solid by filtration. (m.p. 105°–107° C.)

Step D

6H-Dibenzo[b,e][1,4]oxathiepin-2-acetic acid

Reflux 2.0 g of the nitrile of Step C in a mixture of 30 ml of 20% aqueous sodium hydroxide and 30 ml of ethanol for four hours. Strip away the alcohol, wash with ethyl acetate and acidify the aqueous phase with hydrochloric acid. Separate the precipitate by filtration. Wash with water and dry. (m.p. 144°–146° C.)

Step E

6H-Dibenzo[b,e][1,4]oxathiepin-2-acetamide

Reflux for 20 minutes a mixture of 5.0 g of the acid of Step D and 40 ml of thionyl chloride. Evaporate to dryness under vacuum. Evaporate twice with 30 ml portions of carbon tetrachloride. Dissolve the residue in 20 ml of tetrahydrofuran and add the solution dropwise to a cooled and stirred saturated solution (ice-bath) of ammonia in 60 ml of tetrahydrofuran. Pass ammonia through the solution simultaneously. Continue stirring at room temperature for an additional 15 minutes. Evaporate the mixture to dryness. Add a mixture of 12 ml of ethanol and 60 ml of water and stir the suspension for 30 minutes. Separate the solids and wash with water, then with ethanol and finally with ether to obtain the title product.

Step F 2-(4-Hydroxy-$\Delta^3$-pyrrolin-3-yl-2,5-dione)-6H-dibenz[b,e][1,4]oxathiepin Stir at room temperature a mixture of 5.118 g of the amide of Step E, 2.939 g of diethyl oxalate, 4.723 g of potassium t-butoxide and 40 ml of dimethylformamide for 6 hours. Pour the reaction mixture into 300 ml of ice-water and extract with 300 ml of ethyl acetate. Acidify with 6N hydrochloric acid and separate the ethyl acetate layer. Wash with saturated sodium chloride solution and dry. Evaporate to dryness and dissolve the residue in warm dioxane. Treat with a slight excess of ammonia and separate the solid by filtration. Wash with dioxane and dry. Suspend the product in water, acidify with 6N hydrochloric acid and extract with ethyl acetate. Wash the extract with saturated sodium chloride solution, dry over magnesium sulfate and evaporate to obtain the title product.

EXAMPLE 24

β-Hydroxyethyl 6H-dibenz[b,e][1,4]oxathiepin-2-carboxylate

To a stirred solution of 1.0 g of 2-chlorocarbonyl-6H-dibenz[b,e][1,4]oxathiepin in 50 ml of methylene chloride, add 3 g of ethylene glycol and stir the mixture for 18 hours at room temperature. Distill off the solvent and excess ethylene glycol under high vacuum (0.1 mm). Chromatograph the residue on a silica gel column (100 g), eluting with 10% ethyl acetate in benzene to obtain the title product.

In a similar manner, substituting another loweralkyldiol such as, for example, trimethylene glycol and 1,4-butanediol and the like for the ethylene glycol, there is obtained the corresponding hydroxyloweralkylester. The corresponding hydroxyloweralkyl 9-carboxylate esters are prepared by substituting 9-chlorocarbonyl 6H-dibenz[b,e][1,4]oxathiepin for the 2-chlorocarbonyl 6H-dibenz[b,e][1,4]oxathiepin employed above.

EXAMPLE 25

β-Dimethylaminoethyl 6H-dibenz[b,e][1,4]oxathiepin-9-carboxylate

Dissolve 1.0 g of 9-chlorocarbonyl-6H-dibenz[b,e][1,4]oxathiepin as prepared in Example 16, Step A, in 10 ml of anhydrous tetrahydrofuran with stirring and add 2 ml of N,N-dimethylethanolamine. Stir at room temperature for 18 hours and strip the mixture to dryness. Partition the residue between ether and dilute hydrochloric acid and separate the aqueous layer. Basify the aqueous layer with aqueous ammonia and extract with ethyl acetate. Evaporate the organic phase and chromatograph the residue over silica-gel eluting with 90% chloroform in methanol to obtain the title product.

In a similar manner, substituting another N,N-diloweralkylaminoloweralkanol such as, for example, diethylethanolamine, 3-N,N-dimethylaminopropan-1-ol, 4-N,N-diethylaminobutan-1-ol and the like, for the N,N-dimethylethanolamine there is obtained the corresponding N,N-diloweralkylaminoloweralkyl ester. The corresponding N,N-diloweralkyl 2-carboxylate esters are prepared by substituting 2-chlorocarbonyl-6H-dibenz[b,e][1,4]oxathiepin for the 9-chlorocarbonyl-6H-dibenz[b,e][1,4]oxathiepin employed above.

EXAMPLE 26

6H-Dibenz[b,e][1,4]oxathiepin-2-N-carboxyloweralkylcarboxamide

Reflux 1.0 g of 2-chlorocarbonyl-6H-dibenz[b,e][1,4]oxathiepin in 20 ml of ethyl acetate containing 2.0 g of glycine for 5 hours. Evaporate the mixture to dryness. Add 30 ml of water to the solid residue and stir at room temperature for one hour. Separate the solid by filtration and recrystallize from ethanol to obtain the title product.

In a similar manner, substituting another amino acid such as, for example, alanine or valine and the like for the glycine, there is obtained the corresponding 2-carboxyloweralkylcarboxamide.

The corresponding 9-carboxyloweralkylcarboxamides are prepared by substituting 9-chlorocarbonyl-6H-dibenz[b,e][1,4]oxathiepin for the 2-chlorocarbonyl-6H-dibenz[b,e][1,4]oxathiepin employed above.

EXAMPLE 27

β-Carboxyethyl 6H-dibenz[b,e][1,4]oxathiepin-2-carboxylate

Dissolve 1.0 g of 2-chlorocarbonyl-6H-dibenz[b,e][1,4]oxathiepin in 20 ml of tetrahydrofuran and add 1.0 g of the sodium salt of β-hydroxypropionic acid. Stir the mixture at room temperature for 18 hours. Filter and evaporate the filtrate to dryness. Recrystallize the solid residue from ethanol to obtain the title product.

In a similar manner, substituting another hydroxyloweralkanoic acid salt such as, for example, an alkali metal salt of hydroxyacetic acid, 3-hydroxybutyric acid and the like, for the β-hydroxypropionic acid sodium salt, there is obtained the corresponding carboxyloweralkyl-2-carboxylate ester. The corresponding carboxyloweralkyl-9-carboxylate esters are prepared by substituting 9-chlorocarbonyl-6H-dibenz[b,e][1,4]oxathiepin for the 2-chlorocarbonyl-6H-dibenz[b,e][1,4]oxathiepin employed above.

EXAMPLE 28

2-(1H-Tetrazol-5-yl-methyl)-6H-dibenz[b,e][1,4]oxathiepin

Add to 25 ml of tetrahydrofuran cooled in an ice-bath 1.59 g (11.9 mmole) of aluminum chloride, 1.33 g (5.25 mmole) of 2-cyanomethyl-6H-dibenz[b,e][1,4]oxathiepin and 1.55 g (23.8 mmole) of sodium azide. Reflux the mixture for 19 hours, cool, dilute with water and acidify. Extract the mixture into ethyl acetate and evaporate. Triturate the residue in ether and separate the title product by filtration. (m.p. 193°–195° C.).

EXAMPLE 29

6H-Dibenz[b,e][1,4]oxathiepin-2-acetic acid-11,11-dioxide

Heat 600 mg of 6H-dibenz[b,e][1,4]oxathiepin-2-acetic acid to 80°–85° C. in a mixture of 30 ml of glacial acetic acid and 5 ml of 30% hydrogen peroxide for 3 hours. Dilute with water to final volume of about 250 ml. Separate the title product by filtration. (m.p. 188°–190° C.).

EXAMPLE 30

N-(Carboxymethyl)-6H-dibenz[b,e][1,4]oxathiepin-2-carboxamide-11,11-dioxide

Step A

N-(Carbomethoxymethyl)-6H-dibenz[b,e][1,4]oxathiepin-2-carboxamide 11,11-dioxide Suspend 1.161 g of the acid of Example 12 in 70 ml THF and add 2.52 ml of triethylamine followed by 0.43 ml of ethylchloroformate. Stir the mixture at room temperature for 5 minutes. Add in portions 1.134 g glycine methyl ester HCl. Stir at room temperature for twenty-five hours. Filter and wash the collected solids with THF. Evaporate the combined THF and filtrate to dryness. Dissolve the residue in methylene chloride, add 10 g silica gel and evaporate the methylene chloride. Place the residue atop a silica gel column and elute with 50:50 ethyl acetate/toluene. Remove the solvent to obtain the title product. (m.p. 169°–172° C.).

Step B

N-(Carboxymethyl)-6H-dibenz[b,e][1,4]oxathiepin-2-carboxamide-11,11-dioxide

Suspend 542 mg of the methyl ester from Step A and 84 mg of lithium hydroxide hydrate in a mixture of 10 ml water and 10 ml THF. Stir at room temperature for 1.5 hours. Dilute the mixture with 20 ml of water acidified with 2N HCl and extract the mixture with ethyl acetate. Wash the ethyl acetate extracts with saturated sodium chloride solution and dry. Evaporate the solution to dryness. Triturate the resulting solid with ether to obtain the title product. (m.p. 235° C.).

EXAMPLE 31

9-Fluoro-6H-dibenz[b,e][1,4]oxathiepin-2-carboxylic acid

Step A

Bis-(2-carboxy-5-nitrophenyl)disulfide

2-Amino-4-nitrobenzoic acid (18 g, 0.1 mole) was added to water (90 ml) and the mechanically stirred slurry was placed in an ice and water bath; there was then added slowly sulfuric acid (30 ml over about 10 min) so that the temperature did not go over 25°; solution did not occur, but the mixture became less viscous; this suspension was cooled down to 5° and stirred at that temperature for 20 minutes. Then there was begun the slow addition of a solution of sodium nitrite (11.7 g, 98%, 0.166 mole) in water (18 ml). The addition was done in small portions over 1 hour, each portion added beneath the surface of the mixture. Toward the end of the addition, frothing occurred. After the addition of the mixture was stirred for a further 1½ hour at 0°. The mixture was filtered and the filtrate kept cold. The cold filtrate was added dropwise to a solution of sodium carbonate (100 g) and ethyl xanthic acid potassium salt (18 g) in water (750 ml) preheated to 50° in an oil bath. The displacement of the diazonium salt was immediate as each drop caused gassing. The resulting red solution was heated up to 70° (internal) and stirred at that temperature for 3 hours. There was then added more Na$_2$CO$_3$ (25 g) and the heating and stirring was continued for 2½ hours. The mixture was allowed to cool to room temperature and stirred overnight.

A small amount of solid had separated and it was filtered off. The filtrate was acidified slowly with conc. HCl affording a sticky solid which was filtered. The crude product was heated in 40 ml acetic acid on a steam bath for ½ hour, then the mixture was allowed to cool and stir at room temperature overnight.

The insolubles were filtered to yield an orange solid, 11.76 g.

The crude product was dissolved in 500 ml boiling acetone. The mixture filtered hot, concentrated until crystallization began; allowed to cool down and stand for a few hours, then filtered to yield the title compound, 44 g, as an orange solid.

Step B

2-Mercapto-4-nitrobenzyl alcohol

The compound of Step A above (9.50 g, 24 mmoles) was dissolved in THF (100 ml) and the mixture placed under N$_2$ atmosphere. There was added slowly a 1.1M BH$_3$/THF solution (50 ml) an the mixture stirred at room temperature overnight. The mixture had become a slurry containing a gelatinous solid. There was next added additional BH$_3$ solution (25 ml) and after 3 hours the solids had dissolved partly and TLC showed a mixture of I and II (the title compound). Additional borane solution (25 ml) was added and the mixture stirred overnight at room temperature. A clear amber solution had formed and TLC showed only product and a new less polar spot. There was added carefully, water (50 ml) and the THF was evaporated away leaving a yellow solid and the aqueous fraction. This was partitioned between EtOAc and in Na$_2$CO$_3$. The organic layer contained the unknown side-product (I) and the aqueous phase contained the title compound. Acidification of the aqeuous phase and extraction with EtOAc afforded the title compound as a yellow solid, 3.07 g.

Step C 3-(2-Hydroxymethyl-5-nitrophenylthio)-4-hydroxybenzoic acid

A mixture of 2-mercapto-4-nitrobenzyl alcohol 9.49 g, 18.86 mmoles), 4-hydroxy-3-iodo-benzoic acid (4.67 g, 17.69 mmoles), red cuprous oxide (1.35 g, 9.44 mmoles) and 1-methyl-2-pyrrolidinone (40 ml) was heated under a N$_2$ atmosphere. The mixture became a thick slurry at 90° but at 130° had become a dark red solution. After ½ hour at 140° TLC showed that the reaction was finished. The mixture was poured onto 2N HCl (200 ml) and after stirring for a few minutes it was extracted 4× with EtOAc. The EtOAc extracts were washed with water, then extracted 4× with 1N NaOH. The aqueous extracts were washed once with EtOAc then acidified and the resulting solid filtered, washed with water and dried to yield 4.65 g of the title compound.

Step D

Methyl 3-(2-hydroxymethyl-5-nitrophenylthio)-4-hydroxy benzoate

The crude acid from Step C above (4.65 g) was refluxed with methanol (250 ml) containing H$_2$SO$_4$ (5 ml). After 5 hours TLC showed no more acid present. The methanol was evaporated away almost completely and there was added water (25 ml) and, carefully, there was added solid NaHCO$_3$ until all of the acid had been neutralized. The ester was extracted into EtOAc (3×) and the combined organics washed with water (3×), dried over Na$_2$SO$_4$ and evaporated to yield the title compound as a brown solid (4.54 g).

Step E

Methyl 9-nitro-6H-dibenz[b,e][1,4]oxathiepin-2-carboxylate

The ester from Step D above (4.54 g, 13.55 mmoles) was dissolved in THF (100 ml) and there was added diethyl azodicarboxylate (3.0 g, 16.4 mmoles); the solution was cooled in an ice and water bath, and there was added slowly a solution of triphenylphosphine (4.25 g, 16.22 mmoles) in THF (30 ml). After the addition, the mixture was stirred in the cold for 15 minutes and the cooling bath was removed. When the temperature had risen to room temperature, TLC showed that the reaction was over, but stirring was continued overnight. The mixture was evaporated to dryness and the residue dissolved in boiling EtOAc (100 ml). The mixture was concentrated to 70 ml by boiling away the solvent. Then the mixture was allowed to cool down to room temperature. After 4 hours the crystalline material was filtered and dried affording the title compound as a yellow fluffy solid. m.p.: 178°–179°. The filtrate was stripped down and the residue dissolved in CH$_2$Cl$_2$ and chromatographed on a column of silica gel, eluting with CH$_2$Cl$_2$; there was obtained 1.2 g of the title compound contaminated with a small amount of more polar material. This was crystallized from EtOAc and there was obtained 0.73 g of the title compound.

Step F

Methyl 9-amino-6H-dibenz[b,e][1,4]oxathiepin-2-carboxylate

The ester from Step E above (2.83 g, 8.93 mmole) was suspended in THF (40 ml) and conc. HCl (8 ml) was added. Next was added stannous chloride dihydrate (6.63 g, 23 mmoles). The mixture was stirred at room temperature overnight. The reaction was not complete so additional SnCl$_2$.2H$_2$O (2 g) was added and stirring was continued for 7 hours, whereupon TLC showed completeness of the reduction. The mixture was diluted with 1N NaOH (100 ml) and EtOAc. The presence of tin salts made extraction difficult so they were filtered through a bed of Celite. The organic extracts (3×) were washed with saturated NaCl solution twice, then dried over Na$_2$SO$_4$ overnight. The solution was then evaporated to an oil (8 g). Addition of water caused separation of an orange solid which was filtered, washed with water and dried to yield the hydrochloride salt of the title compound, m.p.: >200°. The original tin salt and Celite residues were found to contain product; not enough base had been used. They were suspended in 1N NaOH (100 ml) extracted again with EtOAc. The extracts washed with water, dried over Na$_2$SO$_4$ stripped down to an orange solid which was titrated with water and filtered. The solid was dried affording 1.55 g of the title compound, m.p. 155°–157°.

Step G

Methyl 9-fluoro-6H-dibenz[b,e][1,4]oxathiepin-2-carboxylate

The amine ester from Step F above (1.45 g, 5.05 mmoles) was suspended in conc. HCl (21 ml) and the mixture stirred vigorously for 10 minutes at room temperature, then cooled in an ice, salt and water bath. At 5° C. there was begun the addition of a cold solution of sodium nitrite (710 mg, 10.3 mmole) in water (5 ml). This addition was done over 10 minutes, the solution being added in portions below the surface of the reaction mixture. After the addition, the frothing mixture was stirred in the cold for a further 10 minutes then there was added 48% fluoroboric acid (21 ml) precooled. This caused separation of a yellow solid. The suspension was stirred in the cold for 15 minutes then the solid was filtered, washed with cold 24% HBF$_4$ solution and air dried overnight. the slightly damp solid was added portionwise to decalin (15 ml) preheated to 100°. Each addition of a portion caused frothing; after the addition the mixture was stirred at 100° for a further 20 minutes, then the liquid portion was decanted and the insolubles extracted twice with boiling toluene (10 ml). The combined extracts and original decalin solution was cooled and injected as such to a column of silica gel (100 g) packed in toluene. Elution with toluene afforded the title compound as a white solid, 310 mg, m.p.: 131°–132° C.

Step H

9-Fluoro-6H-dibenz[b,e][1,4]oxathiepin-2-carboxylic acid

The ester from Step G above (395 mg) was heated at 50°–55° C. in a mixture of 20% aqueous NaOH (10 ml) and DAG-ethanol (10 ml) for 2 hours. The mixture was concentrated to ½ volume, diluted with water (20 ml). The solids (Na salt of acid) did not dissolve even on warming. The warm mixture was stirred and acidified with 20% aqueous HCl. The resulting suspension was stirred for 20 minutes at room temperature to afford the title compound as a white solid.

EXAMPLE 32

9-Fluoro-6H-dibenz[b,e][1,4]oxathiepin-2-carboxylic acid-11,11-dioxide

Following the procedure of Example 29 but substituting an equivalent amount of the acid of Example 31, Step H, for the acid of Example 23, Step D, there is obtained the title compound.

EXAMPLE 33

8-Fluoro-6H-dibenz[b,e][1,4]oxathiepin-2-carboxylic acid

Following the procedure of Example 31, Steps A–F, but substituting an equivalent amount of 2-amino-5-nitrobenzoic acid for 2-amino-4-nitrobenzoic acid in Step A there were obtained the following compounds:
Step A: 15.72 g of bis-(2-carboxy-4-nitrophenyl)disulfide
Step B: 3.1 g of 2-mercapto-5-nitrobenzyl alcohol
Step C: 4.07 g of 3-(2-hydroxymethyl-4-nitrophenylthio)-4-hydroxy benzoic acid
Step D: 2.64 g of methyl 3-(2-hydroxymethyl-4-nitrophenylthio)-4-hydroxy benzoate, m.p. 180°–183° C.
Step E: 6.15 g of methyl 8-nitro-6H-dibenz[b,e][1,4]oxathiepin-2-carboxylate, m.p. 225°–226° C.
Step F: 144 mg of methyl 8-amino-6H-dibenz[b,e][1,4]oxathiepin-2-carboxylate, m.p. 154°–155° C.
Step G: Methyl 8-diazonium-6H-dibenz[b,e][1,4]oxathiepin-2-carboxylate fluoroborate salt The amino ester from Step F above (780 mg, 2.72 mmoles) was suspended in conc. HCl (10 ml) and the mixture was stirred vigorously at room temperature for 10 minutes. The solid had become a fine suspension. The mixture was cooled in an ice and salt bath and at 0° there was added slowly (over 10 minutes) a cold solution of sodium nitrite (540 mg, 7.83 mmoles) in water (1.5 ml). The mixture turned red-orange and the solids dissolved almost completely, then a new orange solid separated out. The mixture was stirred at 0° C. for 15 minutes then there was added dropwise (10 ml) precooled 48% fluoroboric acid (10 ml). The orange solid became yellow and the resulting suspension was stirred in the cold for 1 hour, then filtered, washed with cold 25% HBF$_4$ solution and air dried overnight affording the title compound (1.46 g) as a yellow solid.

Step H

Methyl 8-fluoro-6H-dibenz[b,e][1,4]oxathiepin-2-carboxylate

The crude diazonium salt from Step G above (1.31 g) was placed in a 50 ml flask, immersed in an oil bath preheated to 105° and a slight vacuum was applied. Within a few moments the solid began to melt and evolve gas. Heating was continued for 20 minutes, then the mixture was cooled and dissolved in THF (all soluble); there was added 5 grams of silica gel, the mixture evaporated to dryness and the solids placed atop a column of 50 g silica gel. Elution with toluene afforded the title compound (170 mg) as a yellow solid, m.p.: 119°–121° C.

Step I

8-Fluoro-6H-dibenz[b,e][1,4]oxathiepin-2-carboxylic acid

The ester from Step H above (200 mg) was stirred at room temperature in a mixture of 20% aqueous NaOH (10 ml) and THF (10 ml) overnight. Very little hydrolysis had occurred. The mixture was brought to reflux. After 6 hours refluxing was stopped; TLC showed mostly product and a residual less polar spot (weak) which seemed to be very slightly different from the starting ester. The biphasic mixture containing solids was allowed to stir at room temperature overnight. The mixture was diluted with water and EtOAc. The aqueous fraction was collected, leaving behind the organic layer and solids. The organic phase was extracted with water and the solids dissolved. The aqueous phases were combined. Some solids came out of solution. The aqueous suspension was warmed on a steam bath to 50° and acidified with 12N HCl. A fluffy white solid came out. The suspension was cooled down to room temperature and filtered. The solid was washed with water and dried affording the title compound (90 mg), m.p.: 278°–280° C.

EXAMPLE 34

8-Fluoro-6H-dibenz[b,e][1,4]oxathiepin-2-carboxylic acid-11,11-dioxide

Following the procedure of Example 29, but substituting an equivalent amount of the acid of Example 33, Step I, for the acid of Example 23, Step D, there is obtained the title compound.

EXAMPLE 35

2-[1-(Pivalyloxy)ethoxycarbonyl]-6H-dibenz[b,e][1,-4]oxathiepin-11,11-dioxide

To a mixture of 204 mg 6H-dibenz[b,e][1,4]oxathiepin-2-carboxylic acid-11,11-dioxide (0.7 mmole) and 1.5 gram of anhydrous potassium carbonate in 10 ml of dimethyl formamide, there was added a solution of 390 mg 1-chloroethyl pivalate (2.3 mmole) in 10 ml of dimethyl formamide. The reaction mixture was stirred at ambient temperature for 24 hours, then it was partitioned between water and ethyl acetate. The crude product obtained from evaporation of the organic phase was chromatographed on a column of silica gel, eluting with dichloromethane, to isolate the ester which was stirred in a small amount of ether for 4 hours then filtered. The yield was 141 mg, m.p.: 136°–137°.

EXAMPLE 36

Methyl 6H-dibenz[b,e][1,4]oxathiepin-2-carboxylate 11,11-dioxide

To a suspension of 350 mg of the acid of Example 12 in 10 ml of methanol add a solution of diazomethane in ether until all of the acid dissolves and a yellow color persists. Evaporate the solvents and crystallize the residue from toluene-hexane to obtain the title compound, m.p. 114°–116°.

Although the instant invention has been described in the foregoing specification in terms of the use of the novel oxathiepins disclosed herein in the treatment and control of human and warm-blooded animal disease conditions characterized by excessive undesirable contractile activity of prostaglandins and prostaglandin biosynthetic intermediates, and particularly of asthma, it will be recognized by those skilled in the art that, in addition to the involvement of contractile prostaglandins in chronic obstructive lung disease (e.g. asthma), prostaglandins play a role in other allergic conditions as well as in inflammation, diarrhea, hypertension, angina, platelet aggregation, cerebral spasm, premature abortion and dismenorrhea. Also the oxathiepins of this invention are potent TXA$_2$ biosynthesis inhibitors, inhibiting platelet aggregation, and can be useful in diseases such as atherosclerosis, and myocardial infarction. Applicants consider application of the oxathiepins disclosed and claimed herein to the treatment and control of such disease conditions to be obvious equivalents to the invention as disclosed by applicants and to fall within the scope of the instant invention.

Certain of the compounds of the present invention can be separated into optically active (+) and (−) isomers. In such cases, the present invention includes both the racemic as well as the resolved forms of the compound, simply by naming the compound itself.

The subject matter which applicants regard as their invention, and which is sought to be patented herein, is particularly pointed out and distinctly claimed as follows.

What is claimed is:

1. A compound selected from the group consisting of 6H-dibenz[b,e][1,4]oxathiepins having the structural formulae:

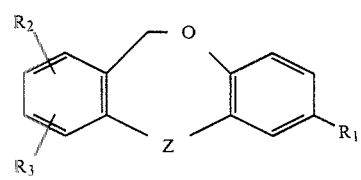

-continued

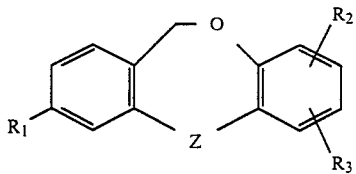

wherein Z is a member selected from the group consisting of thio, sulfinyl, and sulfonyl; $R_2$ and $R_3$ are the same or different and are members selected from the group consisting of hydrogen, halogen, nitro, loweralkyl, amino, N-loweralkylamino, N,N-diloweralkylamino, loweralkanoyl, hydroxy, loweralkoxy, loweralkylthio, trifluoromethylthio, loweralkylsulfinyl, loweralkylsulfonyl, and trifluoromethyl; and $R_1$ is 3-hydroxy-1,2,5-thiadiazol-4-yl; and the pharmaceutically acceptable salt thereof.

2. A compound of claim 1 having the name; 2-(3-Hydroxy-1,2,5-thiadiazol-4-yl)-6H-dibenz[b,e][1,4]oxathiepin.

3. A compound of claim 1, wherein Z is thio.

4. A compound of claim 1, wherein Z is thio; $R_2$ is selected from hydrogen, amino, nitro or fluoro; $R_3$ is hydrogen.

5. A compound of claim 4, wherein $R_2$ is hydrogen.

6. A compound of claim 1, wherein Z is sulfinyl; $R_2$ is selected from hydrogen, amino, nitro or fluoro; $R_3$ is hydrogen.

7. A compound of claim 6, wherein $R_2$ is hydrogen.

8. A compound of claim 1, wherein Z is sulfonyl; $R_2$ is selected from hydrogen, amino, nitro or fluoro; $R_3$ is hydrogen.

9. A compound of claim 8, wherein $R_2$ is hydrogen.

* * * * *